(12) United States Patent
Thompson et al.

(10) Patent No.: US 8,293,720 B2
(45) Date of Patent: Oct. 23, 2012

(54) SUBSTITUTED 4-{3-[6-AMINO-9-(3, 4-DIHYDROXY-TETRAHYDRO-FURAN-2-YL)-9H-PURIN-2-YL]-PROP-2-YNYL}-PIPERIDINE-1-CARBOXYLIC ACID ESTERS AS $A_{2A}R$ AGONISTS

(75) Inventors: Robert D Thompson, Charlottesville, VA (US); Anthony Beauglehole, Charlottesville, VA (US); Frank Schmidtmann, Charlottesville, VA (US); Jayson M. Rieger, Charlottesville, VA (US)

(73) Assignee: Dogwood Pharmaceuticals, Inc., Charlottesville, VA (US)

( * ) Notice: Subject to any disclaimer, the term of this patent is extended or adjusted under 35 U.S.C. 154(b) by 615 days.

(21) Appl. No.: 12/338,369

(22) Filed: Dec. 18, 2008

(65) Prior Publication Data

US 2009/0162292 A1    Jun. 25, 2009

Related U.S. Application Data

(60) Provisional application No. 61/015,303, filed on Dec. 20, 2007.

(51) Int. Cl.
*A01N 43/04* (2006.01)
*A61K 31/70* (2006.01)
*C07H 19/173* (2006.01)

(52) U.S. Cl. ............... 514/46; 514/42; 514/43; 514/45; 536/27.6

(58) Field of Classification Search ............... None
See application file for complete search history.

(56) References Cited

U.S. PATENT DOCUMENTS

| | | | |
|---|---|---|---|
| 6,232,297 B1 | 5/2001 | Linden et al. | |
| 7,214,665 B2 | 5/2007 | Linden et al. | |
| 7,576,069 B2 * | 8/2009 | Rieger et al. | 514/46 |
| 7,589,076 B2 * | 9/2009 | Rieger et al. | 514/46 |
| 7,888,329 B2 * | 2/2011 | Rieger et al. | 514/46 |
| 8,058,259 B2 * | 11/2011 | Thompson et al. | 514/46 |
| 2006/0040888 A1 | 2/2006 | Rieger et al. | |
| 2007/0270373 A1 | 11/2007 | Rieger et al. | |
| 2008/0262001 A1 * | 10/2008 | Kranenburg et al. | 514/263.22 |

OTHER PUBLICATIONS

Michael R. Myers et al., Potent Quinoxaline-Based Inhibitors of PDGF Receptor Tyrosine Kinase Activity. Part 1: SAR Exploration and Effective Bioisosteric Replacement of a Phenyl Substituent, Bioorganic & Medicinal Chemistry Letters, 2003, 13, 3091-3095.

* cited by examiner

*Primary Examiner* — Traviss C McIntosh, III

(57) ABSTRACT

The present invention provides substituted 4-{3-[6-amino-9-(3,4-dihydroxy-tetrahydro-furan-2-yl)-9H-purin-2-yl]-prop-2-ynyl}-piperidine-1-carboxylic acid esters and pharmaceutical compositions containing the same that are selective agonists of $A_{2A}$ adenosine receptors (ARs). These compounds and compositions are useful as pharmaceutical agents.

30 Claims, No Drawings

SUBSTITUTED 4-{3-[6-AMINO-9-(3,4-DIHYDROXY-TETRAHYDRO-FURAN-2-YL)-9H-PURIN-2-YL]-PROP-2-YNYL}-PIPERIDINE-1-CARBOXYLIC ACID ESTERS AS $A_{2A}R$ AGONISTS

STATEMENT OF GOVERNMENT RIGHTS

This invention was made with the assistance of government support under United States Grant No. 1 R41AR052960 and United States Grant No. 1 R 41 AI 071496-01 from the National Institutes of Health. The government may have certain rights to the invention.

FIELD OF THE INVENTION

The present invention relates to substituted 4-{3-[6-amino-9-(3,4-dihydroxy-tetrahydro-furan-2-yl)-9H-purin-2-yl]-prop-2-ynyl}-piperidine-1-carboxylic acid esters and pharmaceutical compositions that are selective agonists of $A_{2A}$ adenosine receptors (ARs). These compounds and compositions are useful as pharmaceutical agents.

BACKGROUND OF THE INVENTION

There has been progressive development of compounds that are more and more potent and/or selective as agonists of $A_{2A}$ adenosine receptors (AR) based on radioligand binding assays and physiological responses. For example, U.S. Pat. No. 6,232,297 to Linden, et al. describes compounds having the general formula:

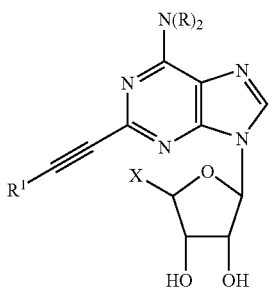

wherein each R can be H, X can be ethylaminocarbonyl and $R^1$ can be $R^1$ can be 4-methoxycarbonylcyclohexylmethyl (DWH-146e). These compounds are reported to be $A_{2A}$ agonists.

U.S. Pat. No. 7,214,665 to Linden, et al. describes compounds having the general formula:

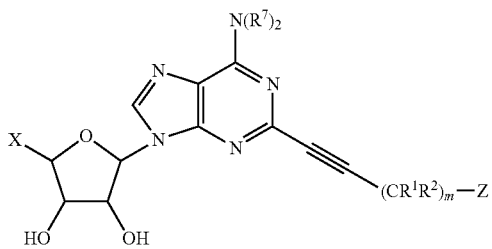

wherein $R^7$ can be H, X can be an ether or an amide, $CR^1R^2$ can be $CH_2$, and Z can be a heterocyclic ring. These compounds are reported to be $A_{2A}$ agonists.

U.S. Pat. Appl. No. 2006/004088 to Rieger, et al. describes compounds having the general formula:

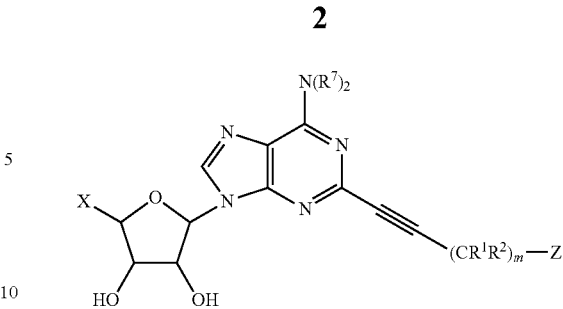

wherein $R^7$ can be H, X can be a cycloalkyl-substituted ether or amide, $CR^1R^2$ can be $CH_2$, and Z can be a heterocyclic ring. These compounds are reported to be $A_{2A}$ agonists.

U.S. Pat. Appl. No. 2007/0270373 to Rieger, et al. describes compounds having the general formula:

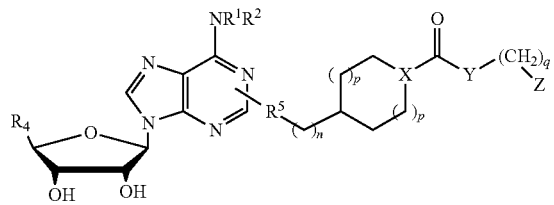

wherein $NR^1R^2$ can be $NH_2$, $R^4$ can be a an ether or an amide, $R^5$ can be ethynyl, Y can be O or $NR^1$, and Z can be an aryl or heteroaryl. These compounds are reported to be $A_{2A}$ agonists.

Even in view of the above, there is a continuing need exists for $A_2$ adenosine receptor agonists useful for therapeutic applications.

SUMMARY OF THE INVENTION

The present invention provides substituted 4-{3-[6-amino-9-(3,4-dihydroxy-tetrahydro-furan-2-yl)-9H-purin-2-yl]-prop-2-ynyl}-piperidine-1-carboxylic acid esters or stereoisomers or pharmaceutically acceptable salts that act as agonists of $A_{2A}$ adenosine receptors.

The present invention also provides pharmaceutical compositions comprising a compound of the present invention or stereoisomer or a pharmaceutically acceptable salt thereof in combination with a pharmaceutically acceptable excipient.

The present invention provides novel methods of treatment and diagnosis compounds and compositions of the present invention.

The present invention provides a novel compound of the present invention for use in medical therapy.

The present invention also provides the use of a novel compound of the present invention for the manufacture of a medicament for the treatment of a pathological condition or symptom in a mammal that the $A_{2A}$ receptor is implicated and for which agonism of the receptor provides therapeutic benefit.

These and other aspects of the present invention have been accomplished in view of the discovery of substituted 4-{3-[6-amino-9-(3,4-dihydroxy-tetrahydro-furan-2-yl)-9H-purin-2-yl]-prop-2-ynyl}-piperidine-1-carboxylic acid esters described herein.

DETAILED DESCRIPTION OF THE INVENTION

The present invention provides novel substituted 4-{3-[6-amino-9-(3,4-dihydroxy-tetrahydro-furan-2-yl)-9H-purin- 2-yl]-prop-2-ynyl}-piperidine-1-carboxylic acid esters that act as agonists at the adenosine $A_{2A}$ receptor, and methods for using the compounds in methods of treating diseases and conditions in which the $A_{2A}$ receptor is implicated and for which agonism of the receptor provides therapeutic benefit. The compounds may be used, for example, for the treatment of inflammatory activity in mammalian tissue, or for the treatment of sickle cell disease. The inflammatory tissue activity can be due to pathological agents or can be due to physical, chemical or thermal trauma, or the trauma of medical procedures, such as organ, tissue or cell transplantation, angioplasty (PCTA), inflammation following ischemia/reperfusion, or grafting. The compounds of the inventions also may be used in conjunction with other anti-inflammatory treatments or in conjunction with anti-pathogenic agents.

In an embodiment, the present invention provides a novel compound of formula I, II, or III or a stereoisomer or pharmaceutically acceptable salt thereof:

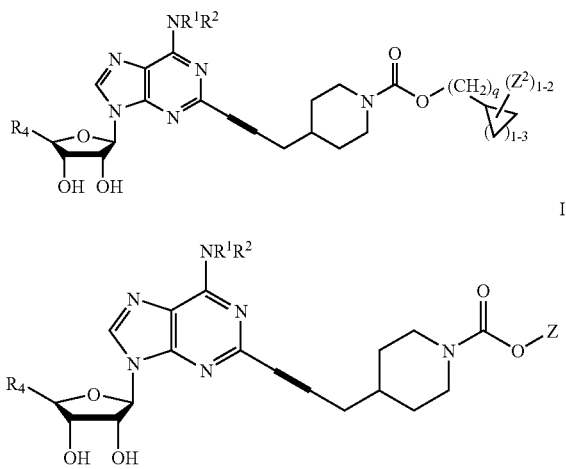

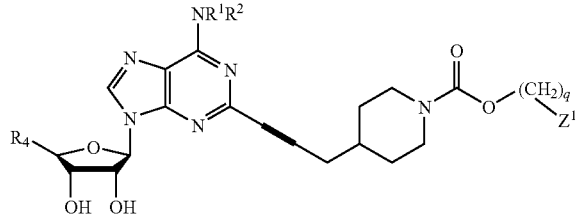

wherein:
$R^1$ and $R^2$ independently are selected from H and $C_{1-3}$ alkyl;

Z is selected from cyclopropyl, cyclobutyl, cyclopentyl, tetrahydrofuranyl, azetidin-2-onyl, pyrrolidinyl, and pyrrolidin-2-onyl;

Z is substituted with 0-2 $Z^2$;

$Z^1$ is selected from tetrahydrofuranyl, azetidin-2-onyl, pyrrolidinyl, and pyrrolidin-2-onyl;

$Z^1$ is substituted with 0-2 $Z^2$;

$Z^2$ is independently selected from F, $C_{1-4}$ alkyl, $CF_3$, $OCF_3$, $(CH_2)_aOR^3$, $(CH_2)_aNR^3R^3$, $NO_2$, $(CH_2)_aCN$, $(CH_2)_aCO_2R^3$, and $(CH_2)_aCONR^3R^3$;

$R^3$ is independently selected from H and $C_{1-6}$ alkyl;

$R^4$ is selected from $CH_2OR$ and $C(O)NRR$;

each R independently is selected from H, $C_{1-4}$ alkyl, cyclobutyl, and $(CH_2)_a$cyclopropyl;

a is selected from 0, 1, and 2; and, q is selected from 1, 2, and 3.

In another embodiment, the present invention provides a novel compound, wherein the compound is of formula I:

$R^1$ and $R^2$ are H;

$Z^2$ is independently selected from F, $C_{1-2}$ alkyl, $CF_3$, $OCF_3$, and $OR^3$;

$R^3$ is independently selected from H and $C_{1-2}$ alkyl;

$R^4$ is C(O)NRR;

each R independently is selected from H, $C_{1-4}$ alkyl, cyclopropyl, cyclobutyl, and —$CH_2$-cyclopropyl; and, q is 1.

In another embodiment, the present invention provides a novel compound, wherein the compound is selected from:

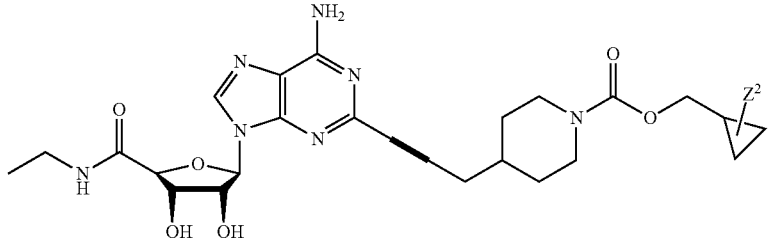

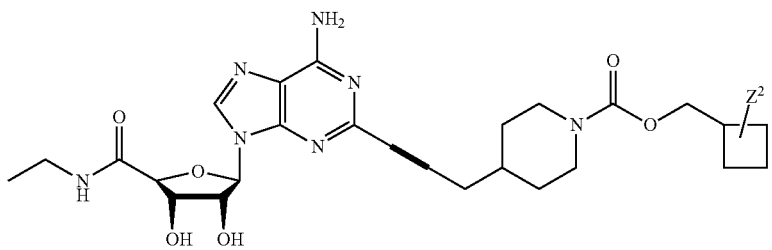

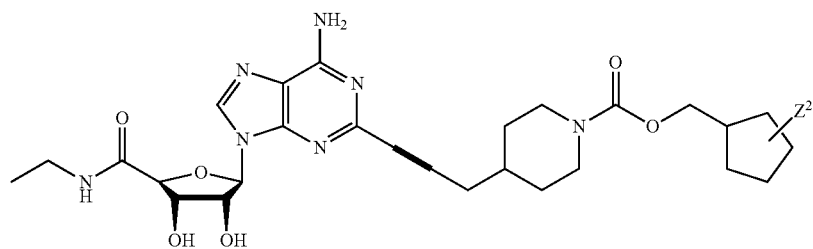

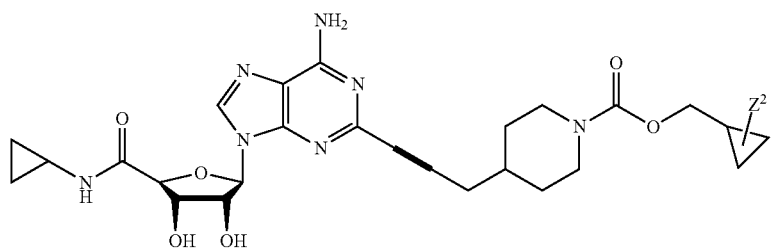

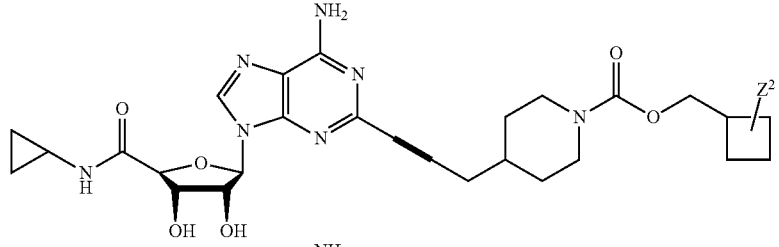

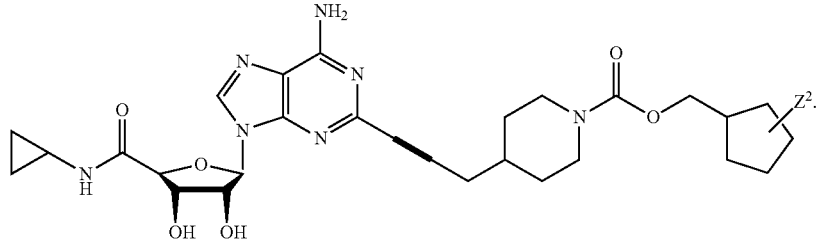

In another embodiment, the present invention provides a novel compound, wherein the compound is of formula II:

$R^1$ and $R^2$ are H;

Z is substituted with 0-1 $Z^2$;

$Z^2$ is independently selected from F, $C_{1-2}$ alkyl, $CF_3$, $OCF_3$, and $OR^3$;

$R^3$ is independently selected from H and $C_{1-2}$ alkyl;

$R^4$ is C(O)NRR; and, each R independently is selected from H, $C_{1-4}$ alkyl, cyclopropyl, cyclobutyl, and —$CH_2$-cyclopropyl.

In another embodiment, the present invention provides a novel compound, wherein the compound is selected from:

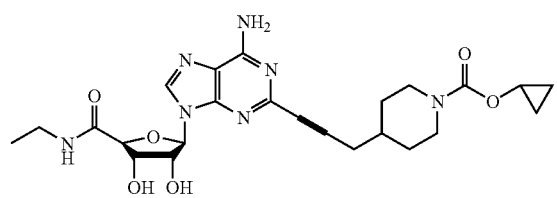

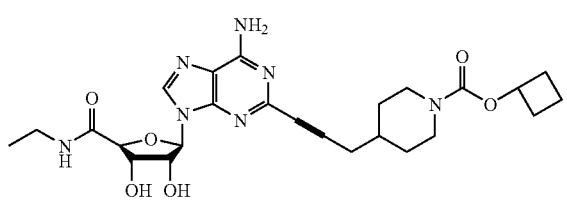

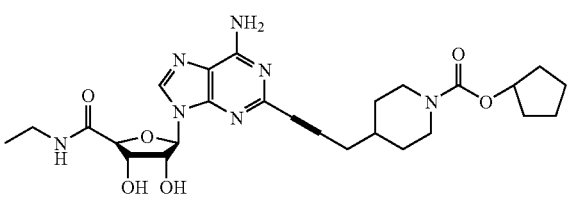

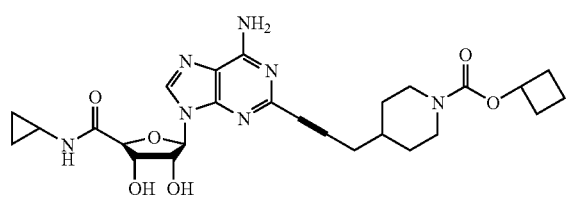
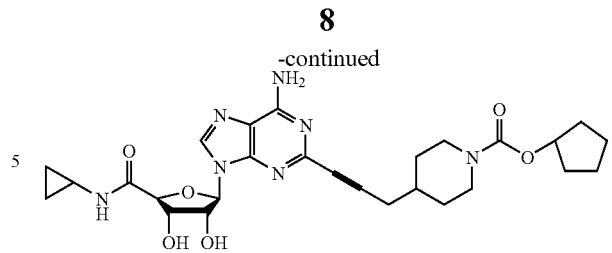
In another embodiment, the present invention provides a novel compound, wherein the compound is selected from:
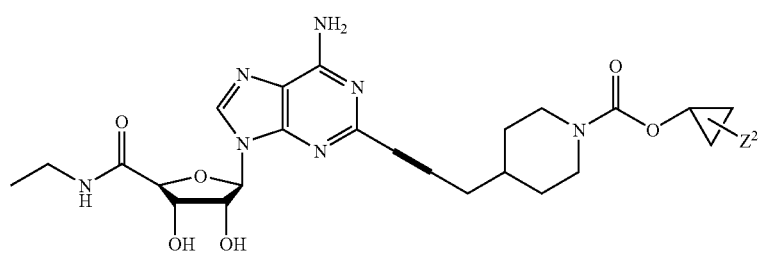
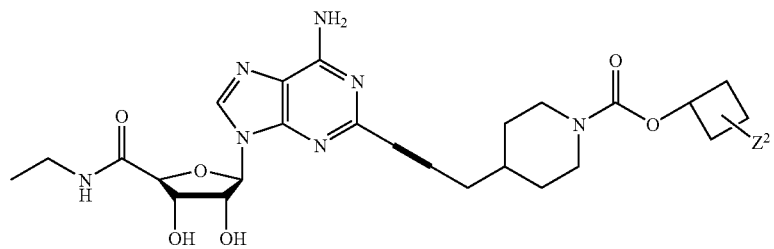
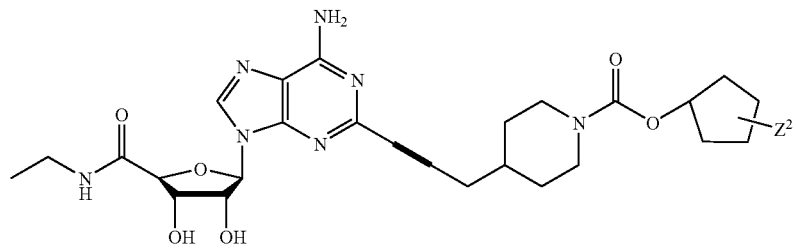
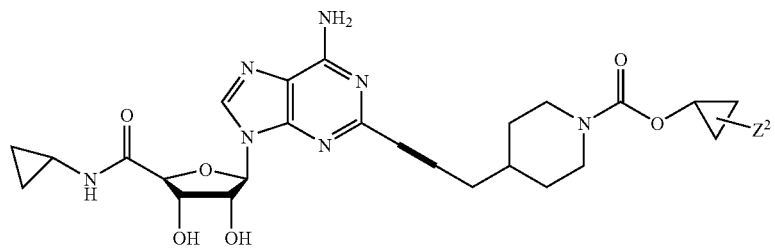
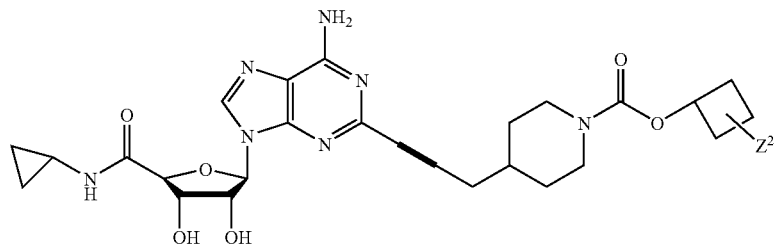

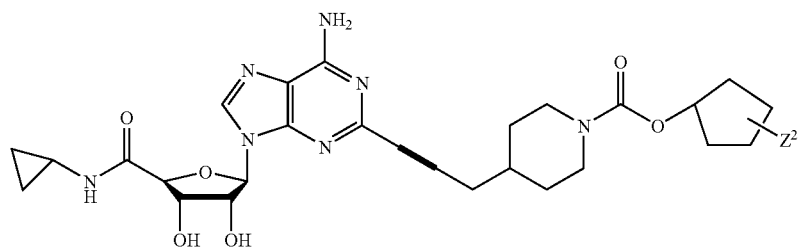

In another embodiment, the present invention provides a novel compound, wherein the compound is of formula III:
R¹ and R² are H;
Z¹ is substituted with 0-1 Z²;
Z² is independently selected from F, $C_{1-2}$ alkyl, $CF_3$, $OCF_3$, and $OR^3$;
R³ is independently selected from H and $C_{1-2}$ alkyl;

R⁴ is C(O)NRR;
each R independently is selected from H, $C_{1-4}$ alkyl, cyclopropyl, cyclobutyl, and —CH₂-cyclopropyl;
q is 0.

In another embodiment, the present invention provides a novel compound, wherein the compound is selected from:

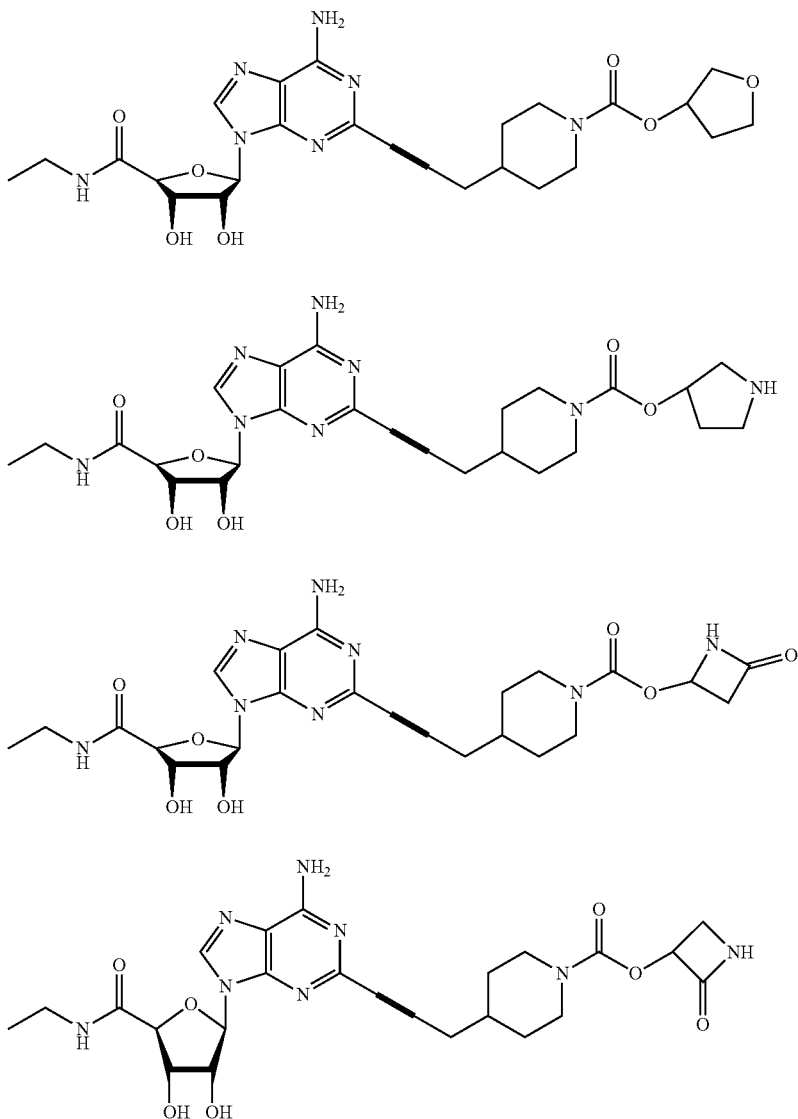

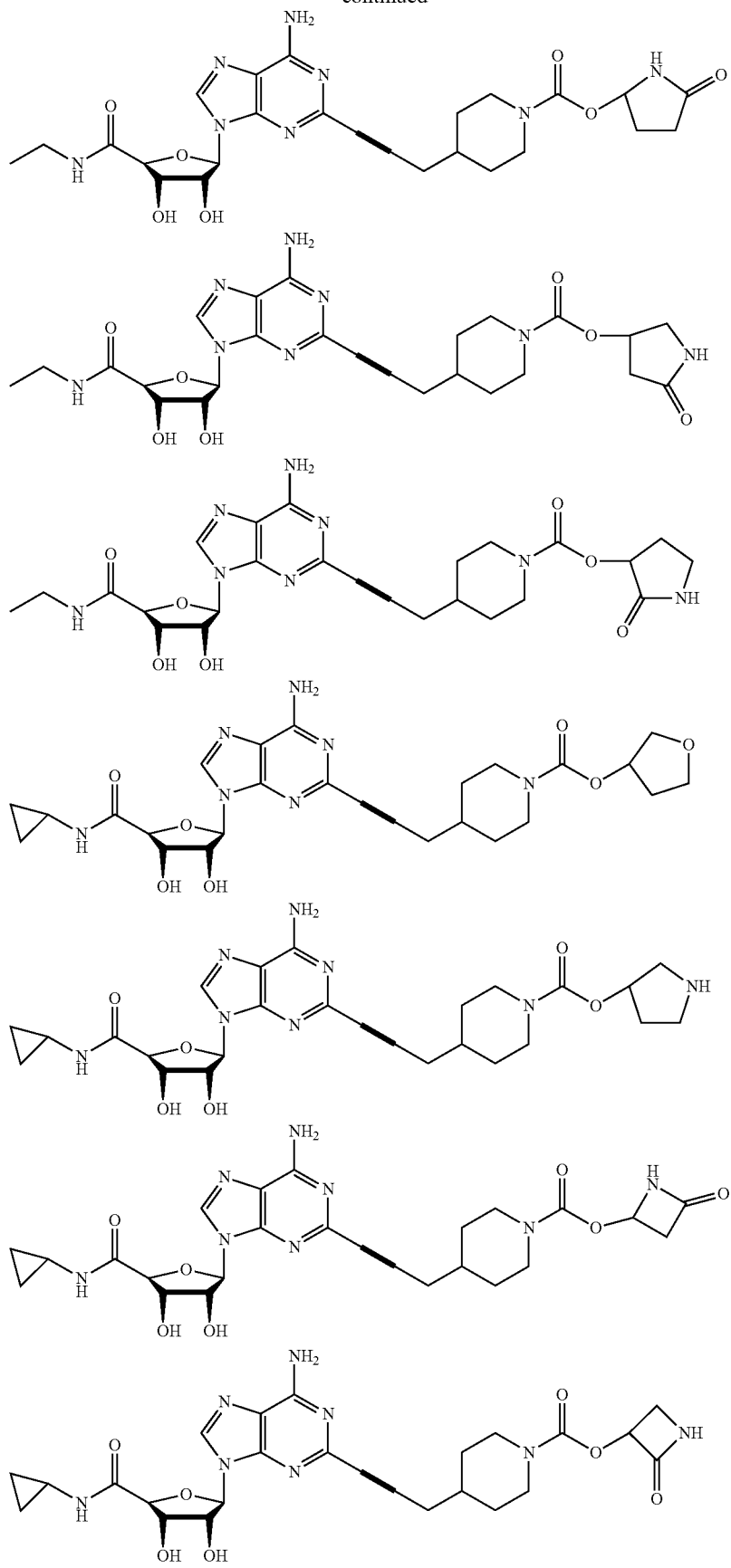

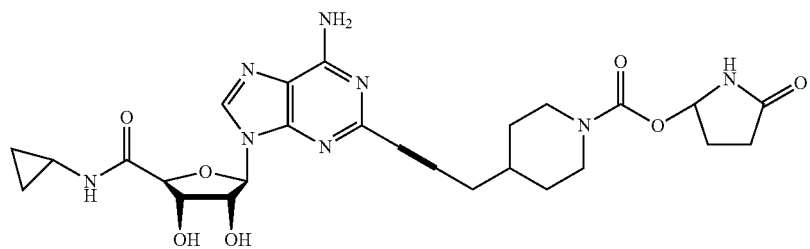
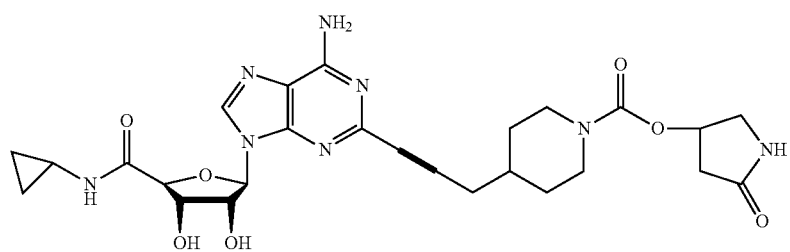
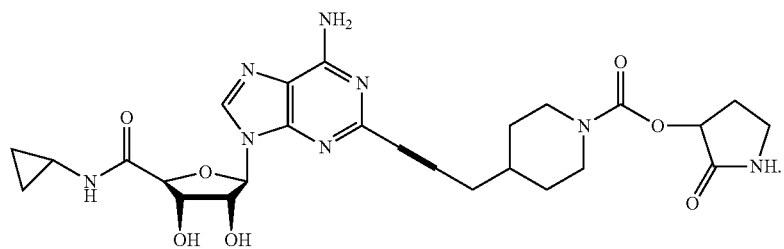
In another embodiment, the present invention provides a novel compound, wherein the compound is selected from:
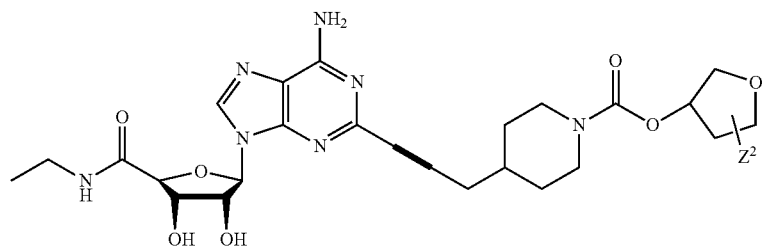
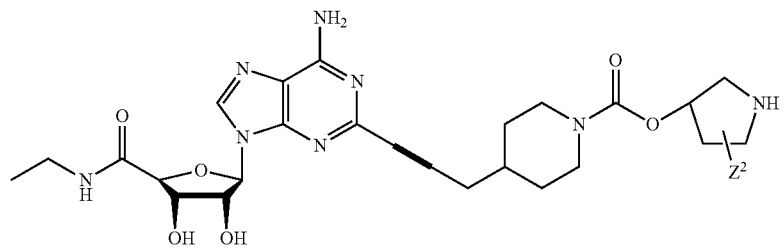
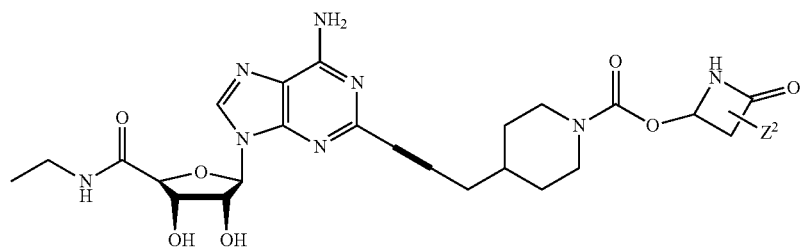

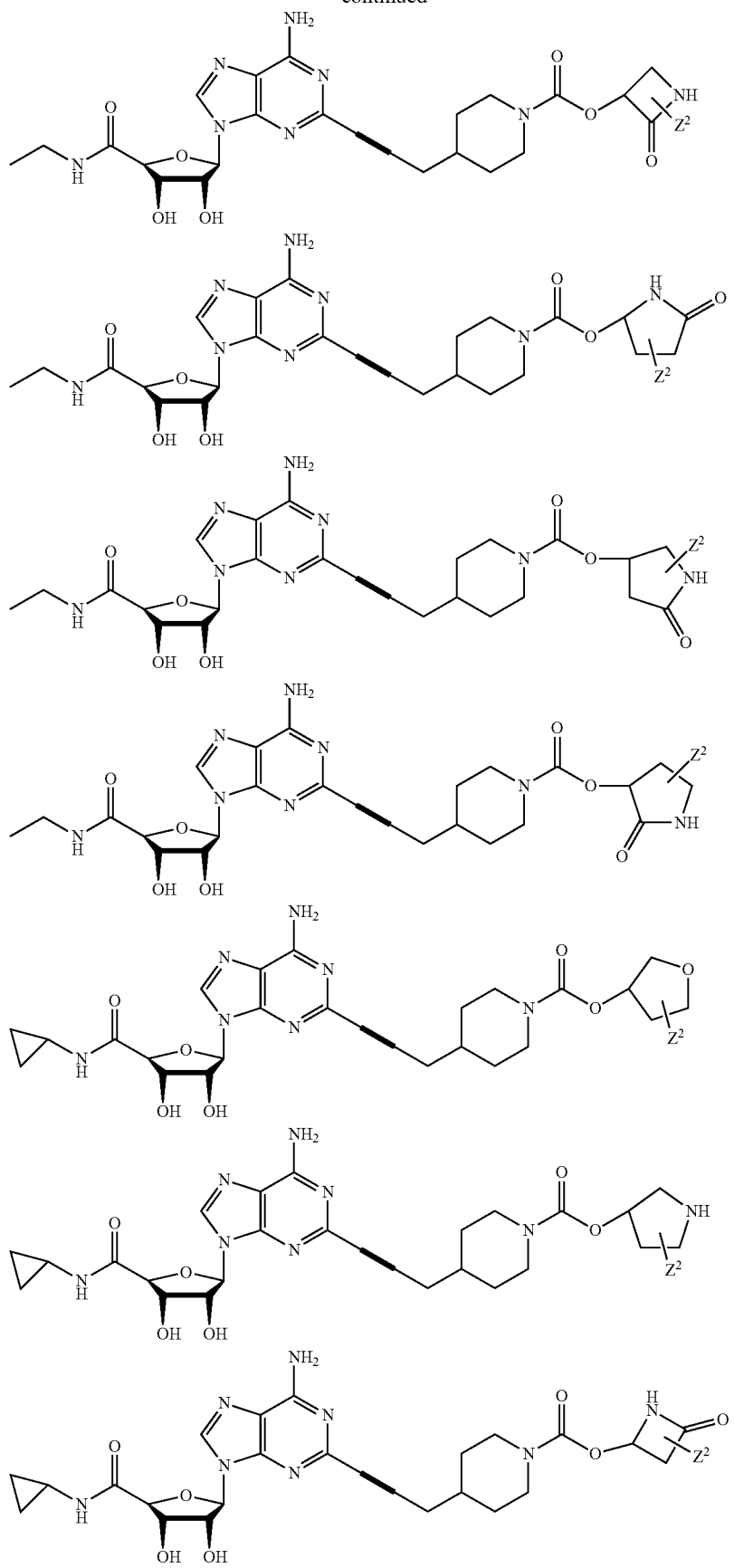

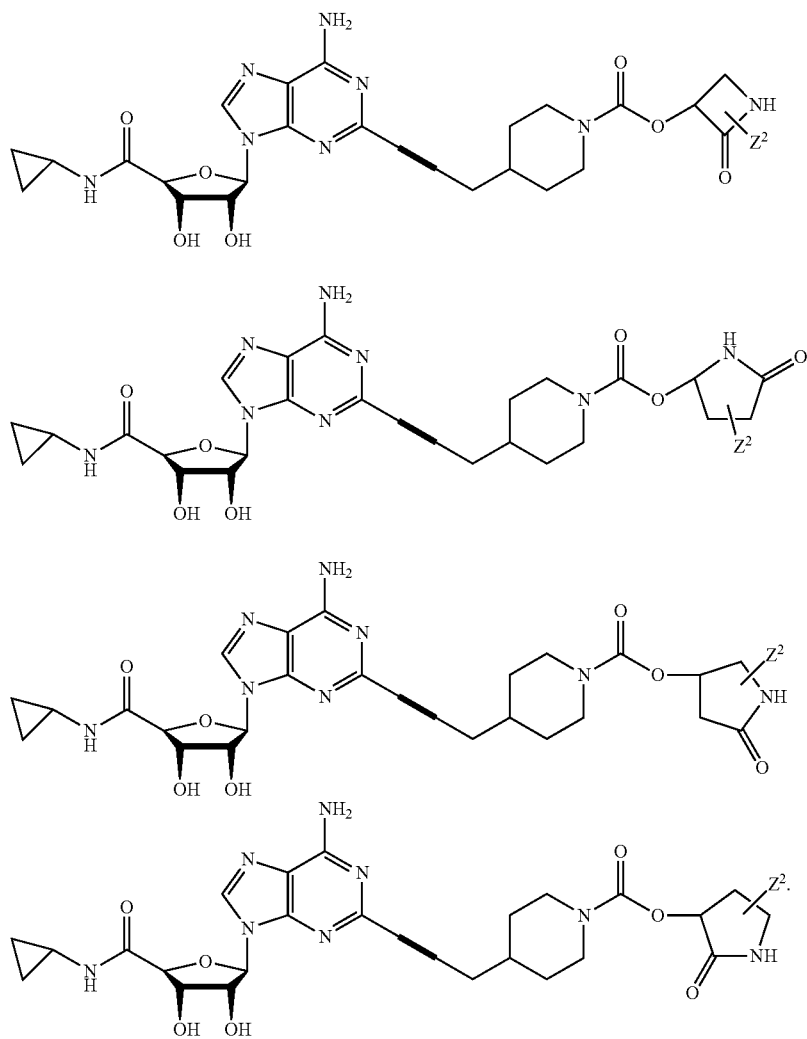
In another embodiment, the present invention provides a novel compound, wherein the compound is selected from:
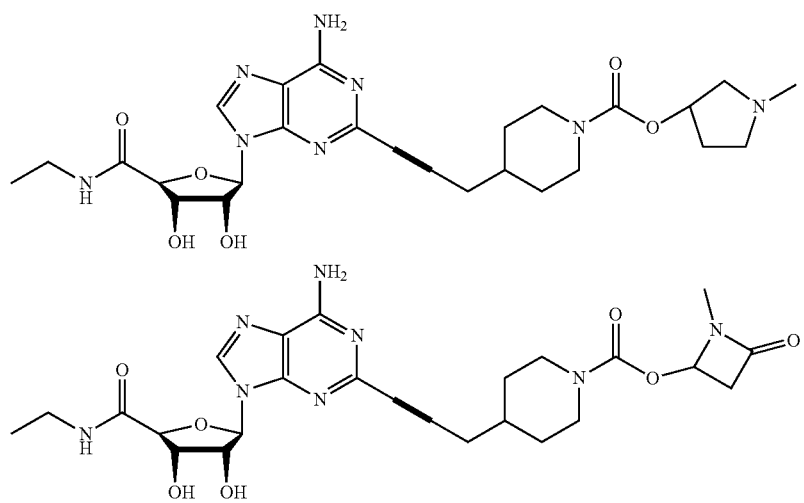

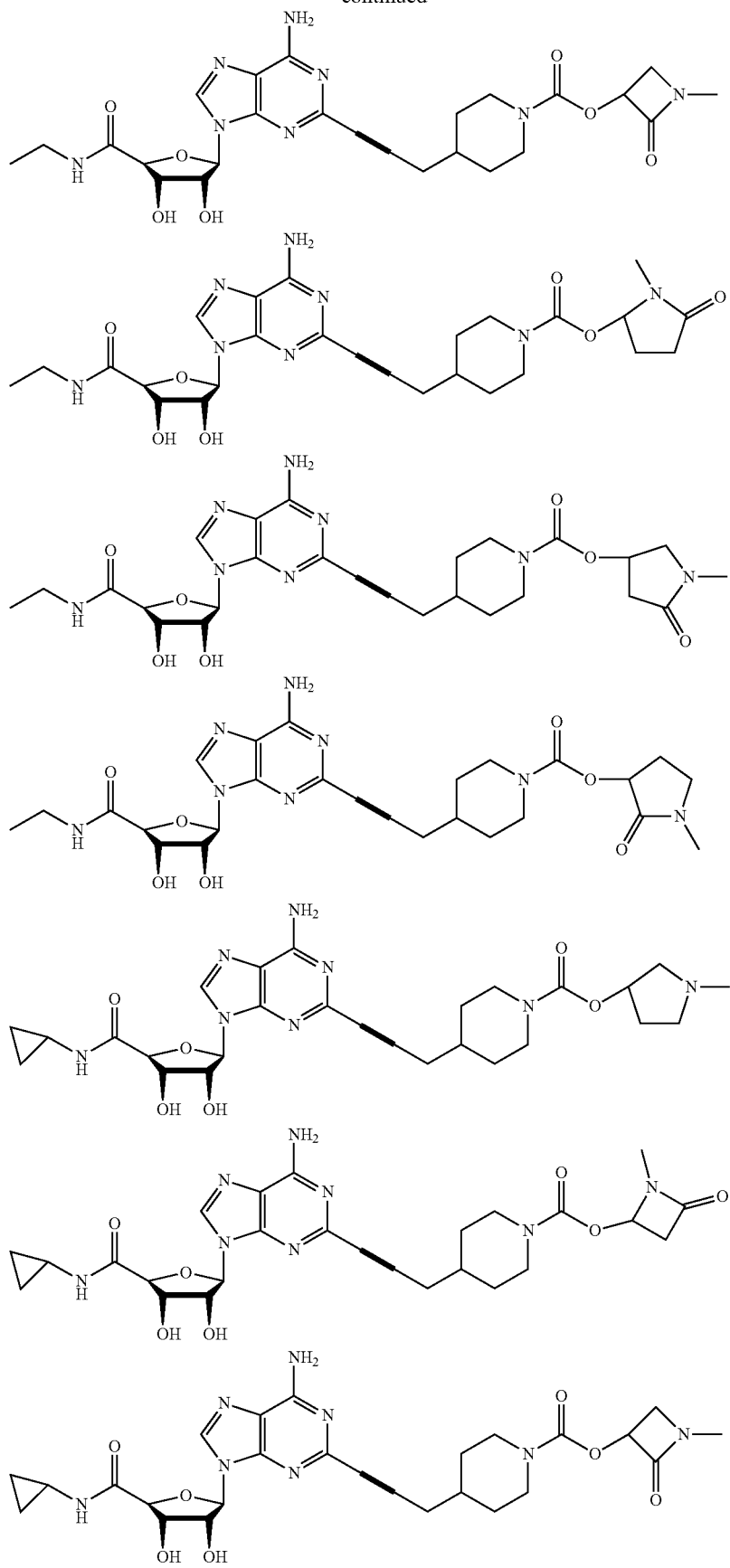

-continued

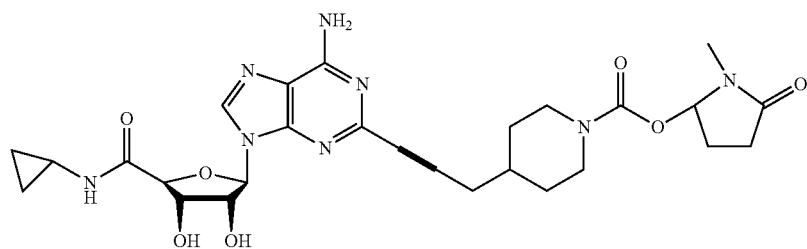

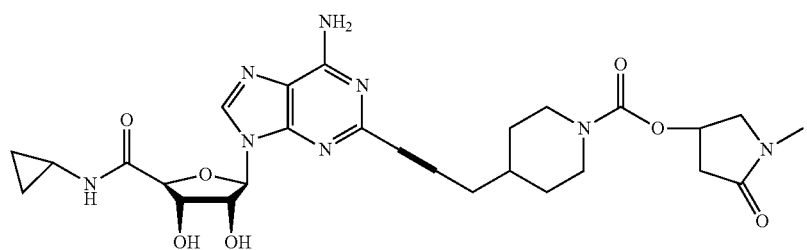

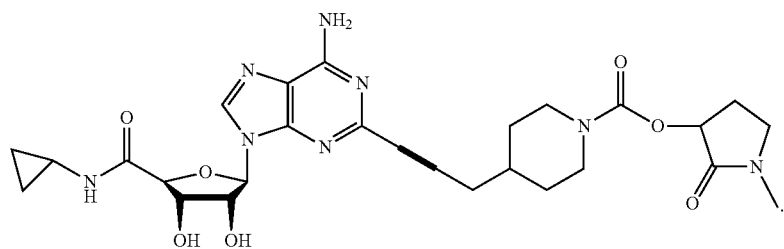

In another embodiment, the present invention provides a novel compound, wherein the compound is of formula III:
$R^1$ and $R^2$ are H;
$Z^1$ is substituted with 0-1 $Z^2$;
$Z^2$ is independently selected from F, $C_{1-2}$ alkyl, $CF_3$, $OCF_3$, and $OR^3$;
$R^3$ is independently selected from H and $C_{1-2}$ alkyl;

$R^4$ is C(O)NRR;
each R independently is selected from H, $C_{1-4}$ alkyl, cyclopropyl, cyclobutyl, and —$CH_2$-cyclopropyl;
q is 1.

In another embodiment, the present invention provides a novel compound, wherein the compound is selected from:

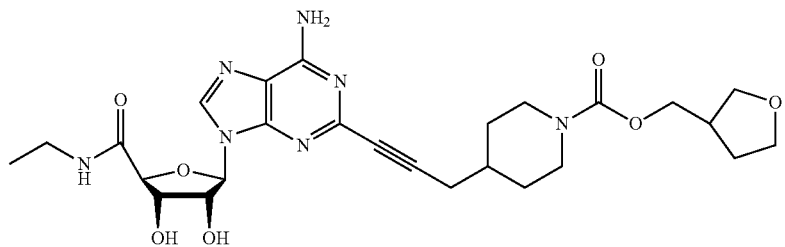

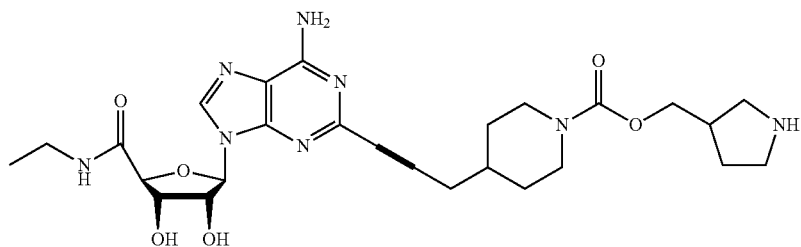

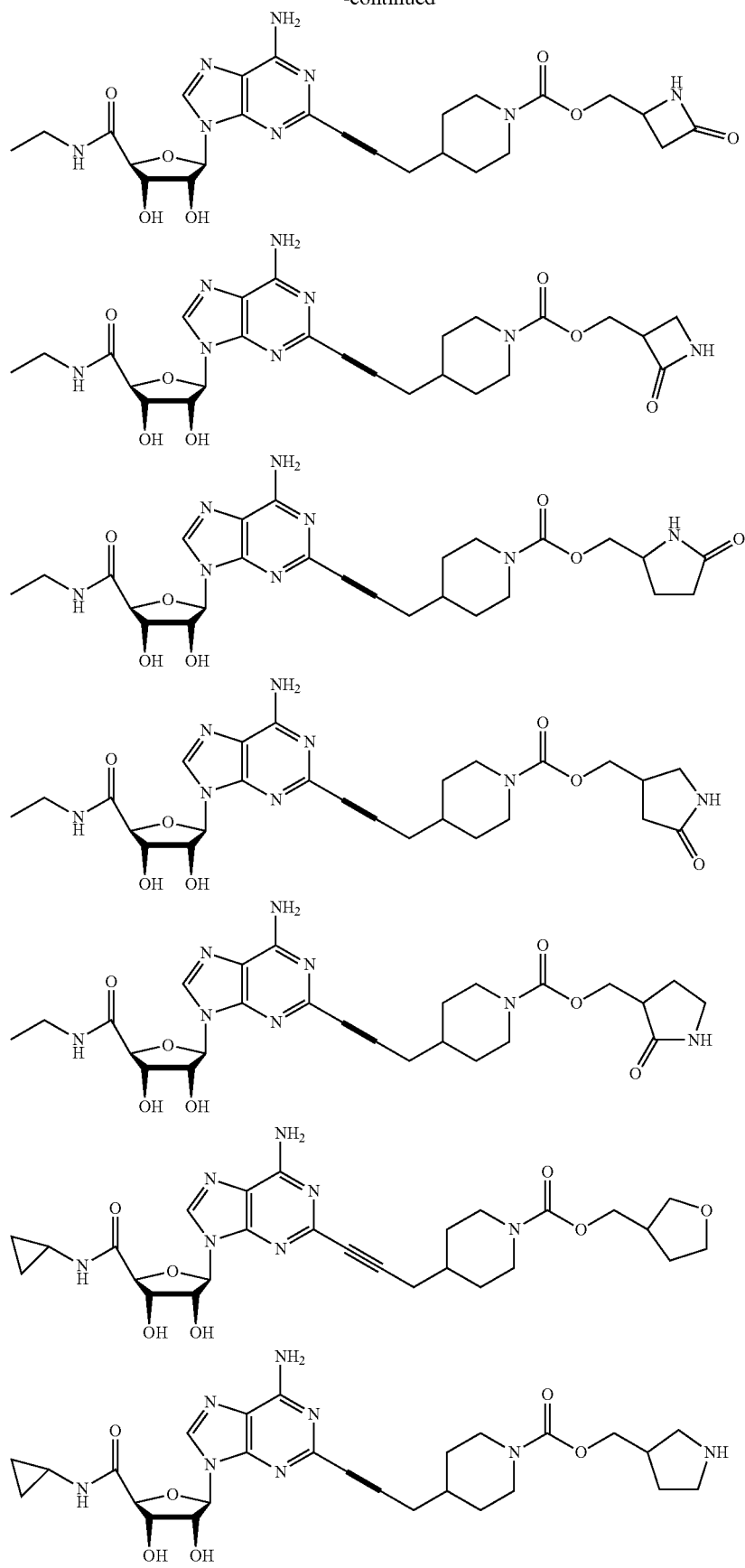

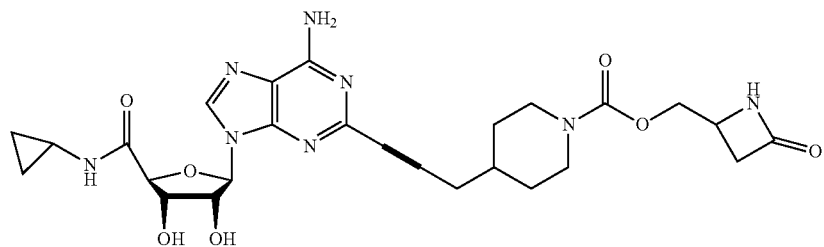
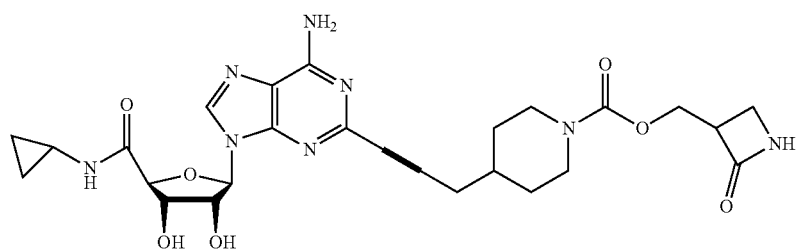
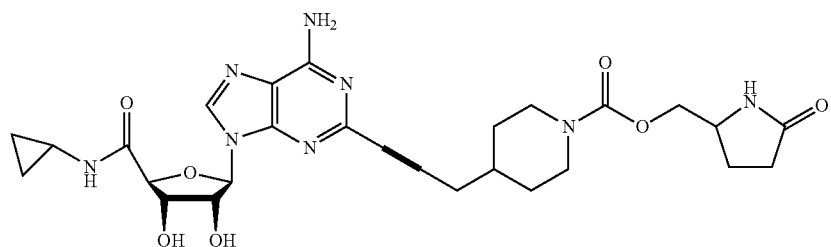
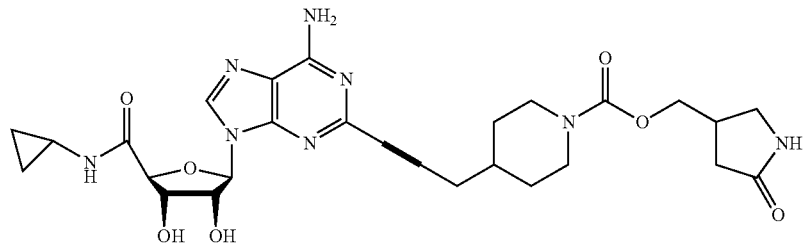
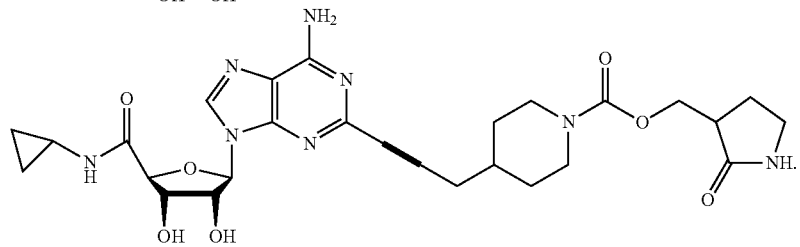
In another embodiment, the present invention provides a novel compound, wherein the compound is selected from:
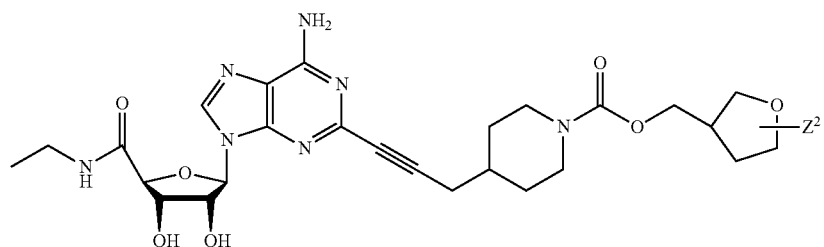

-continued
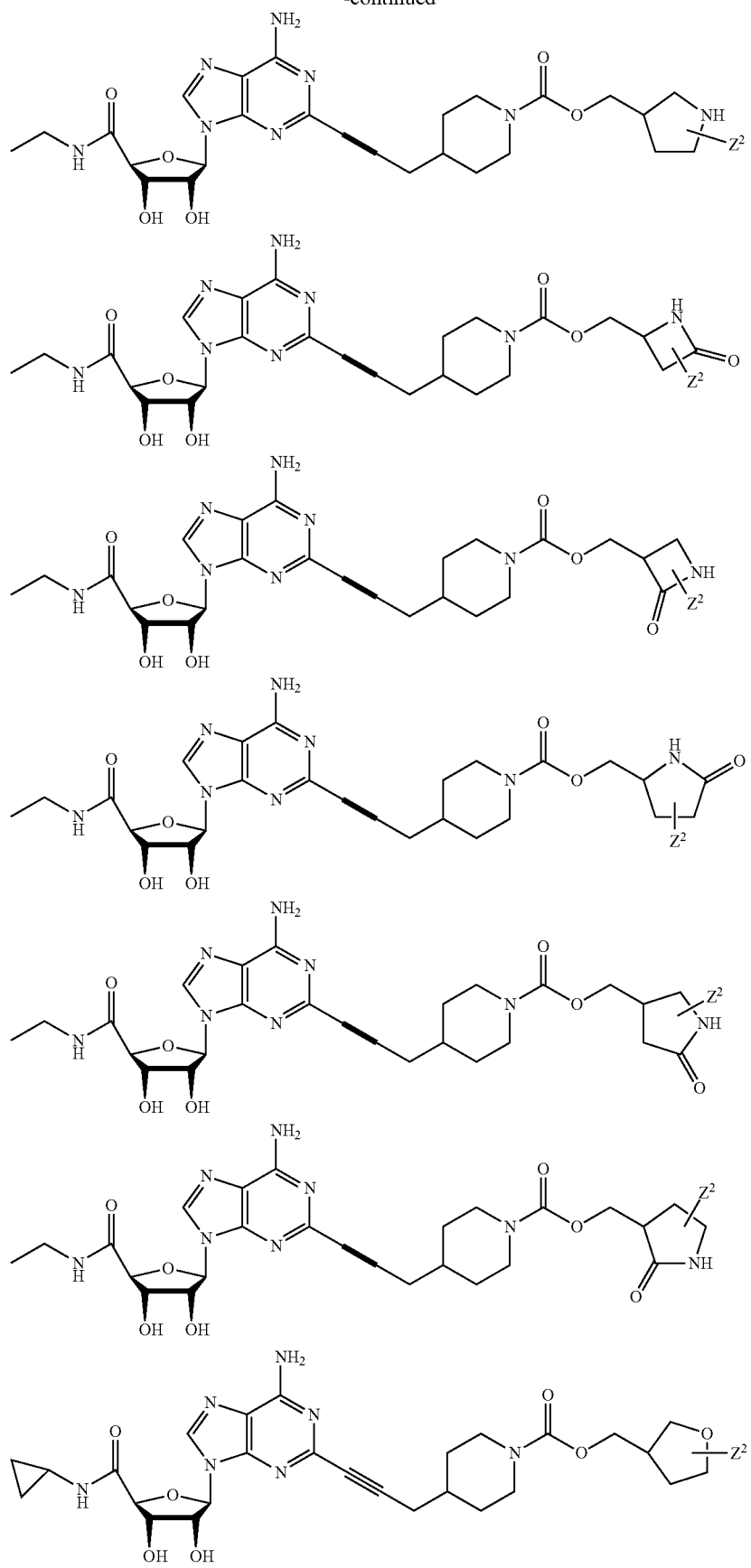

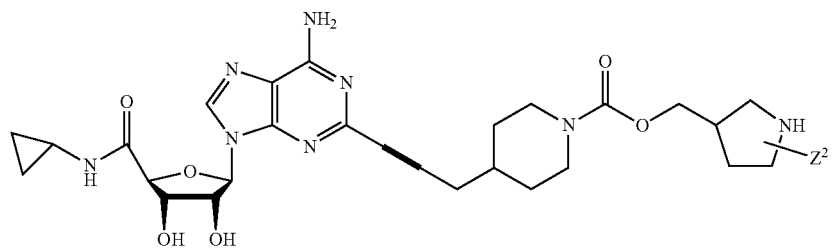
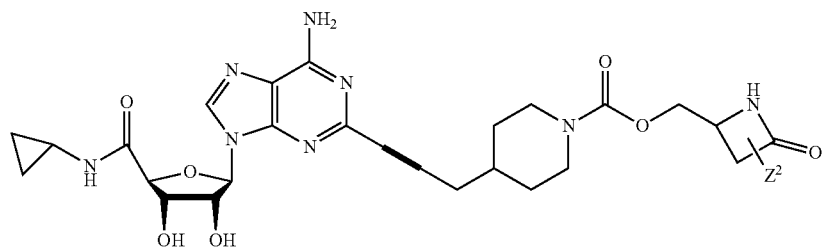
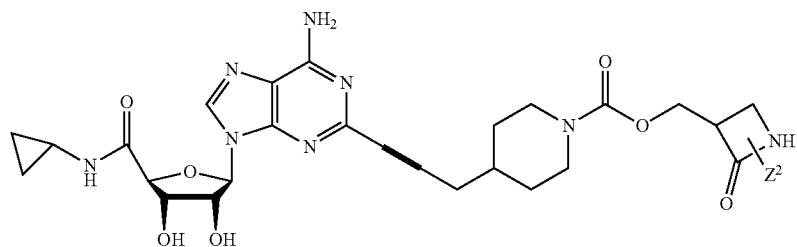
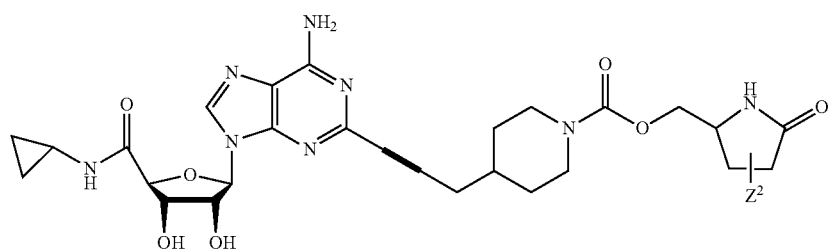
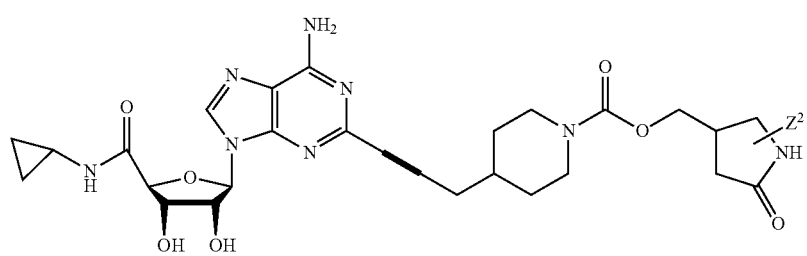
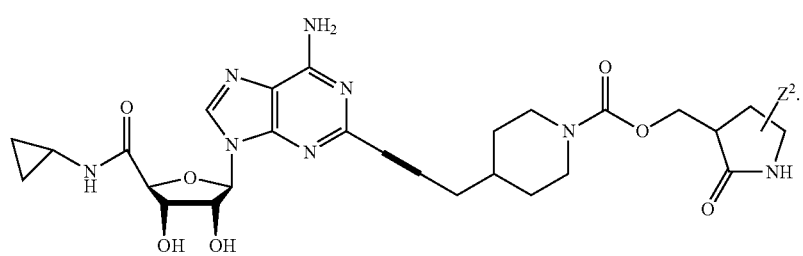

In another embodiment, the present invention provides a novel compound, wherein the compound is selected from:
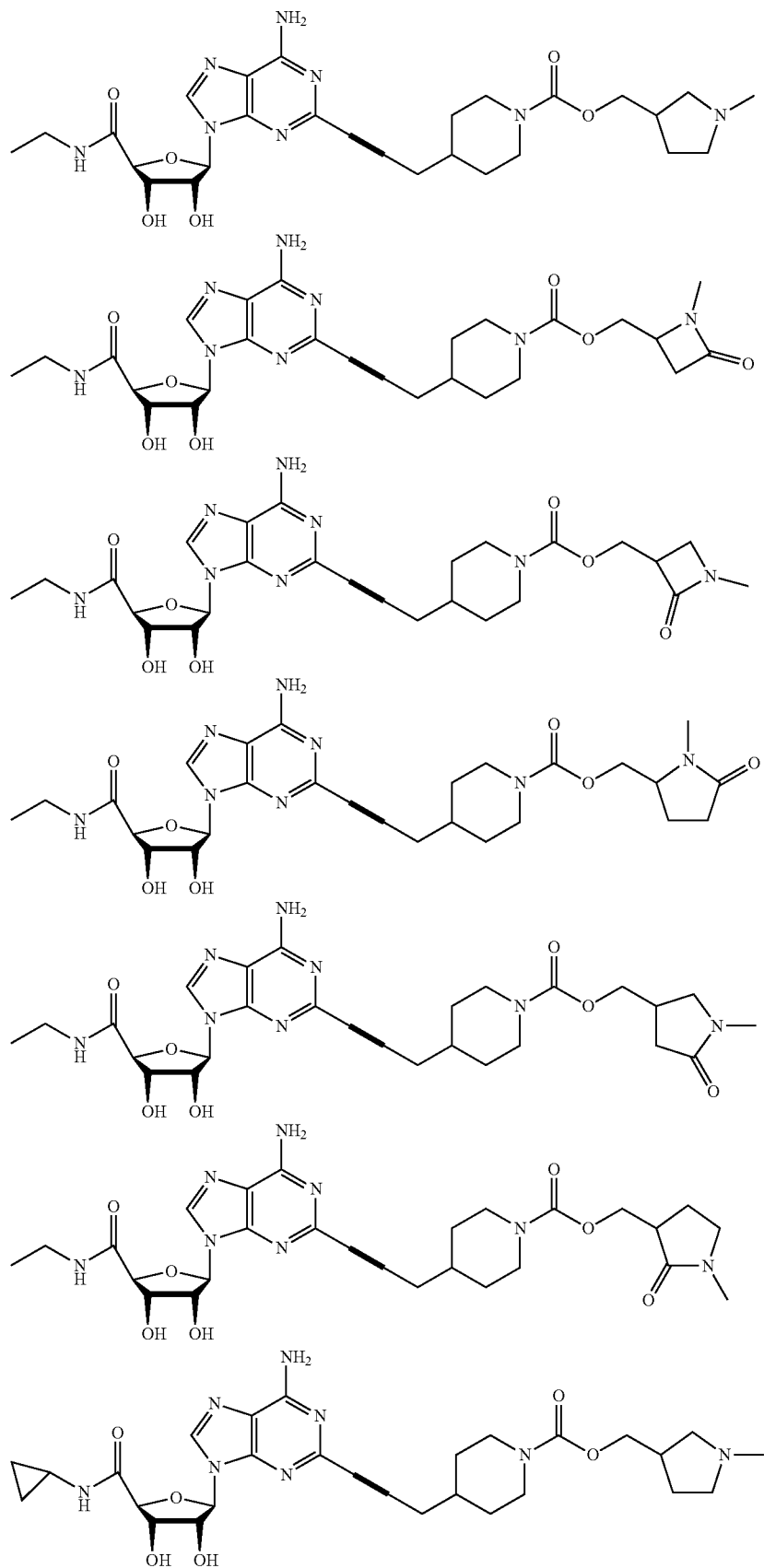

-continued

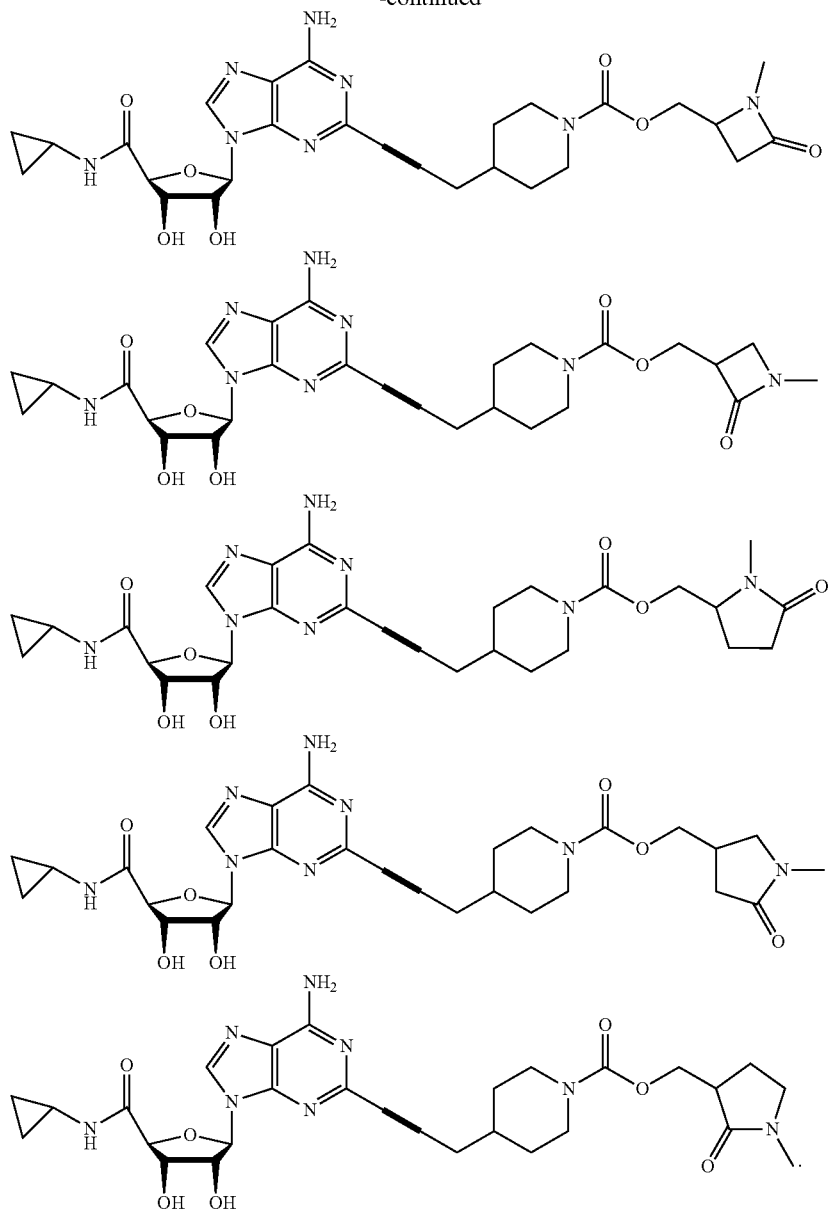

The invention provides a novel compound for use in medical therapy, preferably for use in treating inflammation or protecting mammalian tissue from inflammation such as an inflammatory response, e.g., resulting from allergy, trauma or ischemia/reperfusion injury, as well as the use of a compound of the present invention for the manufacture of a medicament for the treatment of an inflammatory response due to a pathological condition or symptom in a mammal which is associated with inflammation.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The invention also includes the use of a combination of these compounds with at least one anti-inflammatory compound. An example of such a compound is a type IV phosphodiesterase inhibitor, and the combination can be used to cause synergistic decreases in the inflammatory response mediated by leukocytes.

The invention also provides a pharmaceutical composition comprising an effective amount of a compound of the present invention, or a pharmaceutically acceptable salt thereof, in combination with a pharmaceutically acceptable diluent or carrier, and optionally, in combination with an anti-inflammatory compound. The composition can be presented as a unit dosage form. The carrier can be a liquid carrier. The composition can be adapted for oral, intravenous, ocular, parenteral, aerosol or transdermal administration.

The compositions of the present invention may further include a Type IV phosphodiesterase inhibitor, or another anti-inflammatory compound (e.g., other than a PDE inhibitor). The Type IV phosphodiesterase inhibitor may be, for example, rolipram, cilomilast, or roflumilast.

Additionally, the invention provides a therapeutic method for treating a pathological condition or symptom in a mammal where the activity of $A_{2A}$ adenosine receptors is implicated and agonism of said receptors is desired, comprising administering to a mammal in need of such therapy, an effective amount of a compound of the present invention, or a pharmaceutically acceptable salt thereof. It is believed that activation of $A_{2A}$ adenosine receptors inhibits inflammation by affecting neutrophils, mast cells, monocytes/macrophages, platelets T-cells and/or eosinophils. Inhibition of these inflammatory cells results in tissue protection following tissue insults.

In addition, the present invention provides a therapeutic method for treating biological diseases that includes the administration of an effective amount of a suitable antibiotic agent, antifungal agent or antiviral agent in conjunction with an $A_{2A}$ adenosine receptor agonist. If no anti-pathogenic agent is known the $A_{2A}$ agonist can be used alone to reduce inflammation, as may occur during infection with antibiotic resistant bacteria, or certain viruses such as those that cause SARS or Ebola. Optionally, the method includes administration of a type IV PDE inhibitor. The $A_{2A}$ adenosine receptor agonist can provide adjunctive therapy for treatment conditions such as, the inflammation, caused by sepsis, for example, human uremic syndrome when administered with antibiotics in the treatment of bio-terrorism weapons, such as anthrax, tularemia, *Escherichia coli*, plague and the like. The present invention also provides adjunctive therapy for treatment of lethal bacterial, fungal and viral infections such as anthrax, tularemia, *escherichia* and plague comprising administration of an antibacterial agent, an antifungal agent or an antiviral agent in conjunction with selective, $A_{2A}$ adenosine receptor agonists.

The present invention provides a therapeutic method for treating biological diseases that provoke inflammation either alone or in combination with a disease killing medicine. These include bacteria in combination with antibiotics, including but not limited to bacteria that cause anthrax, tularemia, plague, lyme disease and anthrax. Also included are viruses including but not limited to those that cause RSV, severe acute respiratory syndrome (SARS), influenza and Ebola with or without anti-viral therapy. Also included are yeast and fungal infections with or without anti-yeast or anti-fungal agents.

The antibacterial agent, antifungal agent or antiviral agent can be co-administered (e.g., simultaneously) with the $A_{2A}$ adenosine receptor agonist or they can be can be administered either simultaneously or as a mixture or they can be administered subsequently. The subsequent administration of the $A_{2A}$ adenosine receptor agonists can be prior to the agent, within minutes or up to about 48 hours after the administration of the agent. Preferably the administration of the $A_{2A}$ adenosine receptor agonists will be within about 24 hours and more preferably within about 12 hours.

The method of the invention will also be useful for treating patients with sepsis, severe sepsis, and potentially, the systemic inflammatory response syndrome, in addition to septic shock. The $A_{2A}$ adenosine receptor agonists exert multiple anti-inflammatory effects early in the inflammatory cascade, and thus a short course of such agonists can produce profound benefit in serious, life-threatening infectious and inflammatory disorders of humans, including inhalational anthrax, tularemia, *escherichia* and plague.

The anti-inflammatory effect of $A_{2A}$ receptor agonists has been documented in vivo, in experimental models of meningitis, peritonitis and arthritis. The potentially fatal syndrome of bacterial sepsis is an increasingly common problem in acute care units. Sepsis and septic shock, now the eleventh leading cause of death in the United States, are increasing in frequency. Current estimates indicate that about 900,000 new cases of sepsis (approximately 60% Gram negative) occur in the United States annually with an estimated crude mortality rate of 35%. Furthermore, the mortality rate, as assessed in recent clinical trials, is approximately 25%, while approximately 10% of patients die from their underlying disease. Shock develops in approximately 200,000 cases annually with an attributable mortality rate of 46% (92,000 deaths). Sepsis accounts for an estimated $5-10 billion annually in health care expenditures. It is now widely appreciated that among hospitalized patients in non-coronary intensive care units, sepsis is the most common cause of death. Sepsis syndrome is a public health problem of major importance. $A_{2A}AR$ agonists are anticipated to have use as a new and unique adjunctive therapeutic approach to reduce morbidity and mortality. It is believed that this treatment will improve the outcome in systemic anthrax, tularemia, *escherichia* and plague.

The agonists of $A_{2A}$ adenosine receptors of the invention can inhibit neutrophil, macrophage and T cell activation and thereby reduce inflammation caused by bacterial and viral infections. The compounds, in conjunction with antibiotics or antiviral agents can prevent or reduce mortality caused by sepsis or hemolytic uremic syndrome or other inflammatory conditions. The effects of adenosine $A_{2A}$ agonists are enhanced by type IV phosphodiesterase inhibitors such as rolipram.

The invention also provides a compound of the present invention for use in medical therapy (e.g., for use as an adjunct in the treatment of potentially lethal bacterial infections, such as, anthrax, tularemia, *Escherichia*, plague, or other bacterial or viral infections, and treatment of systemic intoxification caused by bacterial and/or viral infections, as well as the use of a compound of the present invention for the manufacture of a medicament for reducing inflammation caused by the bacteria or virus or the treatment thereof in a mammal, such as a human. The compounds of the invention are also useful for treatment of treating systemic intoxification wherein the bacterial or viral agents cause inflammation either directly or as a result of treatment, e.g., with an antibiotic or antiviral agent.

Sepsis is a severe illness caused by overwhelming infection of the bloodstream by toxin-producing bacteria or viruses. The infection, which can manifest as inflammation, can be caused by the bacteria or virus pathogens directly or from the treatment thereof, i.e., the death of the pathogens due to treatment with antibacterial or antiviral agents. Sepsis also can be viewed as the body's response to an infection. The infection can be caused by microorganisms or "germs" (usually bacteria) invade the body, can be limited to a particular body region (e.g., a tooth abscess) or can be widespread in the bloodstream (often referred to as "septicemia" or "blood poisoning")

The systemic intoxification or inflammatory shock is often referred to as Septic shock; Bacteremic shock; Endotoxic shock; Septicemic shock; or Warm shock.

Septic shock is a serious, abnormal condition that occurs when an overwhelming infection leads to low blood pressure and low blood flow. Vital organs, such as the brain, heart, kidneys, and liver may not function properly or may fail. Septic shock occurs most often in the very old and the very young. It also occurs in people with underlying illnesses. Any bacterial organism can cause septic shock. Fungi and viruses may also cause this condition. Toxins released by the bacteria, fungi or viruses may cause direct tissue damage, and may lead to low blood pressure and/or poor organ function. These toxins can also produce a vigorous inflammatory response from the body, which contributes to septic shock.

In another aspect, the present invention also provides a method to treat severe acute respiratory syndrome (SARS), comprising administering to a mammal in need of said therapy, an effective anti-inflammatory amount of an agonists of $A_{2A}$ adenosine receptor, optionally with a PDE-IV inhibitor, such as, rolipram.

The invention also provides methods of treating sickle cell disease by administering the $A_{2A}$ agonists described herein to a subject suffering from sickle cell disease.

The present invention provides compounds and methods of their use for detecting the presence of, and assessing the severity of, coronary artery stenoses in a mammal, such as a human or domestic animal. Preferably, the compounds of the invention are used as pharmacological stress-inducing agents or stressors that are useful in pharmacological stress imaging for the detection and assessment of coronary artery disease. The specific compounds of the invention useful as stress-inducing agents are potent and selective at $A_{2A}$ adenosine receptors, but are also short-acting, so that they are rapidly cleared by the body following the imaging process.

Thus, the present invention provides a method for detecting the presence and severity of coronary artery stenoses in a mammal, such as a human subject, comprising (1) administering an amount of one or more compounds of the present invention and (2) performing a technique on said mammal to detect and/or determine the severity of said coronary artery stenoses.

The invention provides a compound of the present invention for use in medical diagnostic procedures, preferably for use in detecting the presence of, and assessing the severity of, coronary artery stenoses in a human subject. The present invention provides the use of a compound of the present invention for the manufacture of a pharmacologic vasodilator agent which could be used with clinical perfusion imaging techniques for diagnosing and assessing the extent of coronary artery disease. Preferred perfusion imaging techniques are planar or single photon emission computed tomography (SPECT) gamma camera scintigraphy, positron emission tomography (PET), nuclear magnetic resonance (NMR) imaging, magnetic resonance imaging (MRI) imaging, perfusion contrast echocardiography, digital subtraction angiography (DSA) and ultrafast X-ray computed tomography (CINE CT).

The invention also provides a pharmaceutical composition comprising an effective amount of the compound of the present invention, or a pharmaceutically acceptable salt thereof, in combination with a pharmaceutically acceptable diluent or carrier. Preferably, the composition is presented as a unit dosage form, and can be adapted for parenteral, e.g., intravenous infusion.

The following definitions are used, unless otherwise described.

Mammal or subject includes human, equine, porcine, canine, and feline.

The term "substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

Halo is fluoro, chloro, bromo, or iodo.

Alkyl denotes both straight and branched alkyl groups; but reference to an individual radical such as "propyl" embraces only the straight chain radical, a branched chain isomer such as "isopropyl" being specifically referred to. Specifically, $C_{1-6}$ alkyl can be methyl, ethyl, propyl, isopropyl, butyl, isobutyl, sec-butyl, tert-butyl, pentyl, 3-pentyl, neopentyl, hexyl, and the like, in any branched chain form.

Specific and preferred values listed below for radicals, substituents, and ranges, are for illustration only; they do not exclude other defined values or other values within defined ranges for the radicals and substituents.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein the term "in conjunction with" refers to co-administration of an anti-rejection agent with the $A_{2A}$ adenosine receptor agonist. The co-administration of an agent and an $A_{2A}$ adenosine receptor agonists includes administration of the agent and agonist either simultaneously, as a mixture, or sequentially. The sequential administration of the $A_{2A}$ adenosine receptor agonists can be prior to administration of the agent, within minutes or up to about 48 hours either before the administration of the agent. The $A_{2A}$ adenosine receptor agonists can also be administered after the agent. Preferably the administration of the $A_{2A}$ adenosine receptor agonists will be within about 24 hours and more preferably within about 12 hours.

The compounds of the present invention are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours and "rt" for room temperature).

It will be appreciated by those skilled in the art that the compounds of the present invention have more than one chiral center and may be isolated in optically active and racemic forms. Preferably, the riboside moiety of the present invention is derived from D-ribose. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described herein, or using other similar tests which are well known in the art.

Among the inflammatory responses that can be treated (including treated prophylactically) with a compound of the present invention, optionally with a Type IV PDE inhibitor, are inflammation due to: (a) autoimmune stimulation (autoimmune diseases), such as lupus erythematosus, multiple sclerosis, infertility from endometriosis, type I diabetes mellitus including the destruction of pancreatic islets leading to diabetes and the inflammatory consequences of diabetes, including leg ulcers, Crohn's disease, ulcerative colitis, inflammatory bowel disease, osteoporosis and rheumatoid arthritis; (b) allergic diseases such as asthma, hay fever, rhinitis, poison ivy, vernal conjunctivitis and other eosinophil-mediated conditions; (c) skin diseases such as psoriasis, contact dermatitis, eczema, infectious skin ulcers, healing of open wounds, cellulitis; (d) infectious diseases including sepsis, septic shock, encephalitis, infectious arthritis, endotoxic shock, gram negative shock, Jarisch-Herxheimer reaction, anthrax, plague, tularemia, ebola, shingles, toxic shock, cerebral malaria, bacterial meningitis, acute respiratory distress syndrome (ARDS), chronic obstructive pulmonary disease (COPD), lyme disease, HIV infection, (TNFα-enhanced HIV replication, TNFα inhibition of reverse transcriptase inhibitor activity); (e) wasting diseases: cachexia secondary to cancer and HIV; (f) organ, tissue or cell transplantation (e.g., bone marrow, cornea, kidney, lung, liver, heart, skin, pancreatic islets) including transplant rejection, and graft versus host disease; (g) adverse effects from drug therapy, including adverse effects from amphotericin B treatment, adverse effects from immunosuppressive therapy, e.g., interleukin-2 treatment, adverse effects from OKT3 treatment, contrast dyes, antibiotics, adverse effects from GM-CSF treatment, adverse effects of cyclosporine treatment, and adverse effects of aminoglycoside treatment, stomatitis and mucositis due to immunosuppression; (h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes; (i) dialysis, including pericarditis, due to peritoneal dialysis; (j) gout; and (k) chemical or thermal trauma due to burns, acid, alkali and the like.

Additional diseases include equine disorders such as laminitis and founder's disease.

Of particular interest and efficacy is the use of the present compounds to limit inflammatory responses where the ischemia/reperfusion injury is caused by angioplasty or thrombolysis. Also of particular interest and efficacy is the use of the present compounds to limit inflammatory responses due to organ, tissue or cell transplantation, i.e., the transplantation of allogeneic or xenogeneic tissue into a mammalian recipient, autoimmune diseases and inflammatory conditions due to circulatory pathologies and the treatment thereof, including angioplasty, stent placement, shunt placement or grafting. Unexpectedly, it is found that administration of one or more compounds of the present invention is effective after the onset of the inflammatory response, e.g., after the subject is afflicted with a pathology or trauma that initiates an inflammatory response.

Tissue or cells comprising ligand bound receptor sites can be used to measure the selectively of test compounds for specific receptor subtypes, the amount of bioactive compound in blood or other physiological fluids, or can be used as a tool to identify potential therapeutic agents for the treatment of diseases or conditions associated with receptor site activation, by contacting said agents with said ligand-receptor complexes, and measuring the extent of displacement of the ligand and/or binding of the agent, or the cellular response to said agent (e.g., cAMP accumulation).

The following abbreviations have been used herein:
2-Aas 2-alkynyladenosines;
$^{125}$I-ABA $N^6$-(4-amino-3-$^{125}$iodo-benzyl)adenosine
APCI Atmospheric pressure chemical ionization
CCPA 2-chloro-$N^6$-cyclopentyladenosine;
Cl-IB-MECA $N^6$-3-iodo-2-chlorobenzyladenosine-5'-N-methyluronamide;
CPA $N^6$-cyclopentyladenosine
DMF dimethylformamide
DMSO dimethylsulfoxide
DMSO-$d_6$ deuterated dimethylsulfoxide
EtOAc ethyl acetate
eq equivalent
GPCR G protein coupled receptor; h$A_{2A}$AR, Recombinant human $A_{2A}$ adenosine receptor;
IADO 2-Iodoadenosine
$^{125}$I-APE, 2-[2-(4-amino-3-[$^{125}$I]iodophenyl)ethylamino]adenosine;
NECA 5'-N-ethylcarboxamidoadenosine;
IB-MECA $N^6$-3-iodobenzyladenosine-5'-N-methyluronamide;
2-Iodoadenosine 5-(6-amino-2-iodo-purin-9-yl)-3,4-dihydroxytetra-hydro-furan-2-carboxylic acid ethylamide
HPLC high-performance liquid chromatography
HRMS high-resolution mass spectrometry
$^{125}$I-ZM241385, $^{125}$I-4-(2-[7-amino-2-[2-furyl][1,2,4]triazolo[2,3-a][1,3,5]-triazin-5-yl-amino]ethyl)phenol;
INECA 2-iodo-N-ethylcarboxamidoadenosine
LC/MS liquid chromatography/mass spectrometry
m.p. melting point
MHz megahertz
MRS 1220, N-(9-chloro-2-furan-2-yl-[1,2,4]triazolo[1,5-c]quinazolin-5-yl)-2-phenylacetamide;
MS mass spectrometry
NECA N-ethylcarboxamidoadenosine
NMR nuclear magnetic resonance
RP-HPLC reverse phase high-performance liquid chromatography
TBAF tetrabutylammonium fluoride
TBS tert-butyldimethylsilyl
TBDMSCl tert-butyldimethylsilylchloride
TEA triethylamine
TFA trifluoroacetic acid
THF tetrahydrofuran
TLC thin layer chromatography
p-TSOH para-toluenesulfonic acid
XAC 8-(4-((2-aminoethyl)aminocarbonyl-methyloxy)-phenyl)-1-3-dipropylxanthine.

Specific Type IV phosphodiesterase (PDE) inhibitors useful in practicing the instant invention include racemic and optically active 4-(polyalkoxyphenyl)-2-pyrrolidones as disclosed and described in U.S. Pat. No. 4,193,926. Rolipram is an example of a suitable Type IV PDE inhibitor.

The present invention further provides pharmaceutical compositions that include a compound of the present invention in combination with one of more members selected from the group consisting of the following: (a) Leukotriene biosynthesis inhibitors, 5-lipoxygenase (5-LO) inhibitors, and 5-lipoxygenase activating protein (FLAP) antagonists selected from the group consisting of zileuton; ABT-761; fenleuton; tepoxalin; Abbott-79175; Abbott-85761; N-(5-substituted)-thiophene-2-alkylsulfonamides of Formula (5.2.8); 2,6-di-tert-butylphenol hydrazones of Formula (5.2.10); Zeneca ZD-2138 of Formula (5.2.11); SB-210661 of Formula (5.2.12); pyridinyl-substituted 2-cyanonaphthalene compound L-739,010; 2-cyanoquinoline compound L-746,530; indole and quinoline compounds MK-591, MK-886, and BAY×1005; (b) Receptor antagonists for leukotrienes LTB4, LTC4, LTD4, and LTE4 selected from the group consisting of phenothiazin-3-one compound L-651,392; amidino compound CGS-25019c; benzoxazolamine compound ontazolast; benzenecarboximidamide compound BIIL 284/260; compounds zafirlukast, ablukast, montelukast, pranlukast, verlukast (MK-679), RG-12525, Ro-245913, iralukast (CGP 45715A), and BAYx7195; (d) 5-Lipoxygenase (5-LO) inhibitors; and 5-lipoxygenase activating protein (FLAP) antagonists; (e) Dual inhibitors of 5-lipoxygenase (5-LO) and antagonists of platelet activating factor (PAF); (f) Theophylline and aminophylline; (g) COX-1 inhibitors (NSAIDs); and nitric oxide NSAIDs; (h) COX-2 selective inhibitor rofecoxib; (i) Inhaled glucocorticoids with reduced systemic side effects selected from the group consisting of prednisone, prednisolone, flunisolide, triamcinolone acetonide, beclomethasone dipropionate, budesonide, fluticasone propionate, and mometasone furoate; (j) Platelet activating factor (PAF) antagonists; (k) Monoclonal antibodies active against endogenous inflammatory entities; (1) Anti-tumor necrosis factor (TNFα) agents selected from the group consisting of etanercept, infliximab, and D2E7; (m) Adhesion molecule inhibitors including VLA-4 antagonists; (n) Immunosuppressive agents selected from the group consisting of cyclosporine, azathioprine, and methotrexate; or (O) anti-gout agents selected from the group consisting of colchicines.

Examples of pharmaceutically acceptable salts are organic acid addition salts formed with acids that form a physiological acceptable anion, for example, tosylate, methanesulfonate, malate, acetate, citrate, malonate, tartrate, succinate, benzoate, ascorbate, α-ketoglutarate, and α-glycerophosphate. Suitable inorganic salts may also be formed, including hydroCl, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the present invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain: binders, such as gum tragacanth, acacia, corn starch or gelatin; excipients, such as dicalcium phosphate; a disintegrating agent, such as corn starch, potato starch, alginic acid and the like; a lubricant, such as magnesium stearate; and a sweetening agent, such as sucrose, fructose, lactose or aspartame or a flavoring agent, such as peppermint, oil of wintergreen, or cherry flavoring. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially nontoxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients as enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid, a liquid or in a dermatological patch.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions, which can be used to deliver the compounds of the present invention to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949. Useful dosages of Type IV PDE inhibitors are known to the art. For example, see, U.S. Pat. No. 5,877,180, Col. 12.

Generally, the concentration of the compound(s) of the present invention in a liquid composition, such as a lotion, will be from about 0.1-25% wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 µg/kg, e.g., from about 10 to about 75 µg/kg of body weight per day, such as 3 to about 50 µg per kilogram body weight of the recipient per day, preferably in the range of 6 to 90 µg/kg/day, most preferably in the range of 15 to 60 µg/kg/day.

The compound is conveniently administered in unit dosage form; for example, containing 5 to 1000 µg. conveniently 10 to 750 µg, most conveniently, 50 to 500 µg of active ingredient per unit dosage form.

Ideally, the active ingredient should be administered to achieve peak plasma concentrations of the active compound of from about 0.1 to about 10 nM, preferably, about 0.2 to 10 nM, most preferably, about 0.5 to about 5 nM. This may be achieved, for example, by the intravenous injection of a 0.05 to 5% solution of the active ingredient, optionally in saline, or orally administered as a bolus containing about 1-100 µg of the active ingredient. Desirable blood levels may be maintained by continuous infusion to provide about 0.01-5.0 µg/kg/hr or by intermittent infusions containing about 0.4-15 µg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. For example, it is desirable to administer the present compositions intravenously over an extended period of time following the insult that gives rise to inflammation.

The ability of a given compound of the invention to act as an $A_{2A}$ adenosine receptor agonist may be determined using pharmacological models which are well known to the art, or using tests described below.

The present compounds and compositions containing them are administered as pharmacological stressors and used in conjunction with any one of several noninvasive diagnostic procedures to measure aspects of myocardial perfusion. For example, intravenous adenosine may be used in conjunction with thallium-201 myocardial perfusion imaging to assess the severity of myocardial ischemia. In this case, any one of several different radiopharmaceuticals may be substituted for thallium-201 (e.g., technetium-99m-labeled radiopharmaceuticals (ie: Tc-99m-sestamibi, Tc-99m-teboroxime), iodine-123-labeled radiopharmaceuticals such as I-123-IPPA or BMIPP, rubidium-82, nitrogen-13, etc.). Similarly, one of the present compounds may be administered as a pharmacological stressor in conjunction with radionuclide ventriculography to assess the severity of myocardial contractile dysfunction. In this case, radionuclide ventriculographic studies may be first pass or gated equilibrium studies of the right and/or left ventricle. Similarly, a compound of the present invention may be administered as a pharmacological stressor in conjunction with echocardiography to assess the presence of regional wall motion abnormalities. Similarly, the active compound may be administered as a pharmacological stressor in conjunction with invasive measurements of coronary blood flow such as by intracardiac catheter to assess the functional significance of stenotic coronary vessels.

There also is provided a method to diagnose myocardial perfusion abnormalities in a mammal comprising: (a) parenterally administering to said mammal an amount of a compound or composition as described above; and (b) performing a technique on the mammal to detect the presence of coronary artery stenoses, assess the severity of coronary artery stenoses or both. The myocardial dysfunction may be, for example, coronary artery disease, ventricular dysfunction and differences in blood flow through disease-free coronary vessels and/or stenotic coronary vessels. The technique to detect the presence and assess the severity of coronary artery disease may be, for example, radiopharmaceutical myocardial perfusion imaging, ventricular function imaging, or techniques for measuring coronary blood flow velocity. The radiopharmaceutical myocardial perfusion imaging may be, for example, planar scintigraphy, single photon emission computed tomography (SPECT), positron emission tomography (PET), nuclear magnetic resonance (NMR) imaging, perfusion contrast echocardiography, digital subtraction angiography (DSA) and ultrafast X-ray computed tomography (CINE CT). A radiopharmaceutical agent may be used in conjunction with the radiopharmaceutical myocardial perfusion imaging, and the radiopharmaceutical agent may comprise, for example, a radionuclide selected from the group consisting of thallium-201, technetium-99m, nitrogen-13, rubidium-82, iodine-123 and oxygen-15. When the radiopharmaceutical myocardial perfusion imaging is scintigraphy, the radiopharmaceutical agent may be thallium-201. The ventricular function imaging technique may be, for example, echocardiography, contrast ventriculography or radionuclide ventriculography. The method for measuring coronary blood flow velocity may be, for example, doppler flow catheter, digital subtraction angiography and radiopharmaceutical imaging techniques. These methods of diagnosis may also comprise the steps of: (a) administering to the human by intravenous infusion or by bolus injection an amount of a compound or composition as described above to provide coronary artery dilation; (b) administering a radiopharmaceutical agent comprising thallium-201 or technetium-99m to the human; and (c) performing the scintigraphy on the human in order to detect the presence and assess the severity of coronary artery disease. The radiopharmaceutical agent may be, for example, Tc-99m-sestamibi.

The method typically involves the administration of one or more compounds of the present invention by intravenous infusion in doses which are effective to provide coronary artery dilation (approximately 0.25-500, preferably 1-250 mcg/kg/min). However, its use in the invasive setting may involve the intracoronary administration of the drug in bolus doses of 0.5-50 mcg.

Preferred methods comprise the use of a compound of the present invention as a substitute for exercise in conjunction with myocardial perfusion imaging to detect the presence and/or assess the severity of coronary artery disease in humans wherein myocardial perfusion imaging is performed by any one of several techniques including radiopharmaceutical myocardial perfusion imaging using planar scintigraphy or single photon emission computed tomography (SPECT), positron emission tomograph (PET), nuclear magnetic resonance (NMR) imaging, perfusion contrast echocardiography, digital subtraction angiography (DSA), or ultrafast X-ray computed tomography (CINE CT).

A method is also provided comprising the use of a compound of the present invention as a substitute for exercise in conjunction with imaging to detect the presence and/or assess the severity of ischemic ventricular dysfunction in humans wherein ischemic ventricular dysfunction is measured by any one of several imaging techniques including echocardiography, contrast ventriculography, or radionuclide ventriculography. The myocardial dysfunction can be coronary artery disease, ventricular dysfunction, differences in blood flow through disease-free coronary vessels and stenotic coronary vessels and the like.

A method is also provided comprising the use of a compound of the present invention as a coronary hyperemic agent in conjunction with means for measuring coronary blood flow velocity to assess the vasodilatory capacity (reserve capacity) of coronary arteries in humans wherein coronary blood flow velocity is measured by any one of several techniques including Doppler flow catheter or digital subtraction angiography.

The invention will be further described by reference to the following detailed examples, which are given for illustration of the invention, and are not intended to be limiting thereof.

EXAMPLES

Nuclear magnetic resonance spectra for proton ($^1$H NMR) were recorded on a 300 MHz Varian Gemini 2000 (or similar instrument) spectrophotometer. The chemical shift values are expressed in ppm (parts per million) relative to tetramethylsilane. For data reporting, s=singlet, d=doublet, t=triplet, q=quartet, and m=multiplet. Mass spectra were measured on a Finnigan LCQ Advantage. Analytical HPLC was done on a Shimazdu LC10 or LC20 Systemtimes. 150 mm) as described below. Preparative HPLC was performed on a Shimadzu Discovery HPLC with a Shim-pack VP-ODS C18 (20×100 mm) column operated at room temperature. Compounds were eluted at 30 mL/min with a gradient 20-80% of water (containing 0.1% TFA) to methanol over 15 minutes with UV detection at 254 nm using a SPD10A VP Tunable detector. All final compounds presented here were determined to be greater than 98% pure by HPLC. Flash chromatography was performed on Silicyle 60A gel (230-400 mesh) or using reusable chromatography columns and system from RT Scientific, Manchester N.H. All reactions were done under a nitrogen atmosphere in flame-dried glassware unless otherwise stated.

Example 1

4-{3-[6-Amino-9-(5-cyclopropylcarbamoyl-3,4-dihydroxy-tetrahydro-furan-2-yl)-9H-purin-2-yl]-prop-2-ynyl}-piperidine-1-carboxylic Acid Cyclobutyl Ester

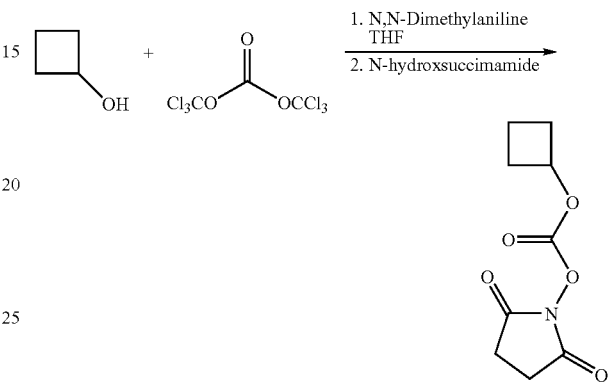

To triphosgene (0.34 eq) stirring in THF at 0° C. under inert atmosphere, the alcohol (1.0 eq) and dimethylaniline (1.1 eq) are added slowly as a solution in dry THF. After ten minutes, the reaction is warmed to room temperature and stirred for an additional 3 h. Dry DCM is then added and the mixture is poured slowly into a solution of N-hydroxysuccinamide (1.3 eq) in dry DCM at 0° C. The reaction is slowly warmed to room temperature and stirred overnight. Water is added to the mixture and after stirring for an additional 3 h, the solution is diluted with EtOAc. The organic layer is washed 3 times with water, once with brine, then dried (MgSO$_4$) and concentrated. The resulting oil (which may be a mixture of the carbonate and symmetrical anhydride) was taken directly onto the next step.

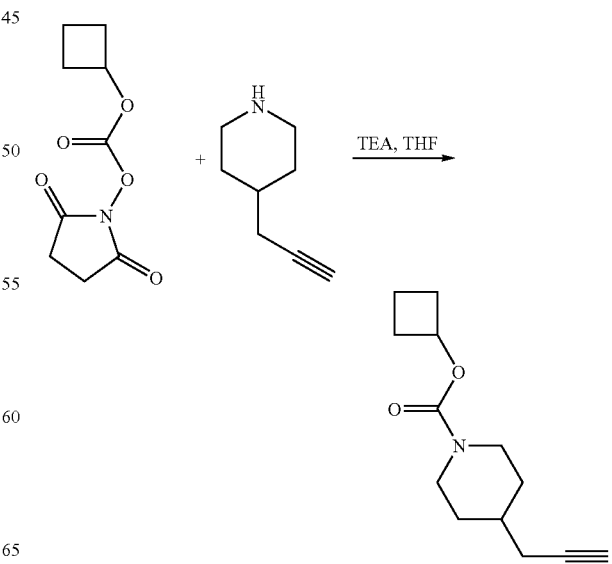

The piperidine derivative (0.75 eq) is dissolved in dry THF and TEA (excess) is added slowly at room temperature under inert atmosphere. The carbonate compound (1.0 eq) is diluted with THF and added dropwise to the piperidine solution. The mixture is stirred for 24 h then concentrated for application to silica gel chromatography (gradient starting at 100% hexanes up to 80% DCM in hexanes). The resulting oil (60% yield) is stored at 4° C. until further use.

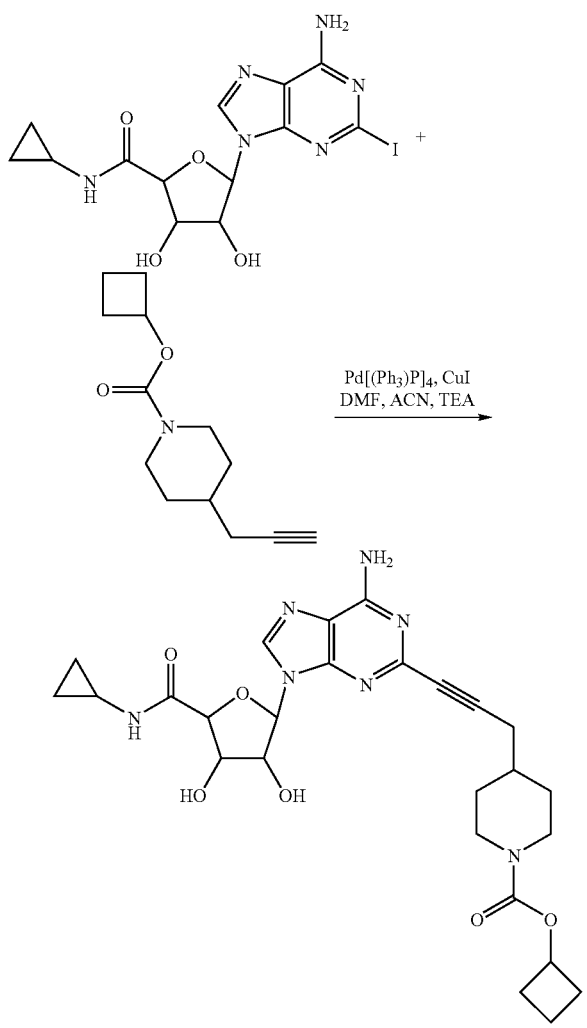

Iodo derivative (1.0 eq) is dissolved in a solution of DMF: ACN:TEA 5:5:1 (all solvent vigorously degassed) and stirred at room temperature under inert atmosphere. Palladium catalyst (~5 mol %) and copper [I] iodide (1.05 eq) are added followed by the alkyne derivative (4.0 eq). The resulting dark solution is stirred overnight then concentrated for application to silica gel chromatography (gradient starting at 100% DCM up to 10% MeOH in DCM). The resulting oil was further purified by preparative HPLC to obtain an off white solid (~30% yield).

$^1$H NMR (DDMSO) δ 8.56 (s, 1H), 8.30 (s, 1H), 7.52 (s, 2H), 5.97 (d, 1H, J=6.6), 5.67 (dd, 2H, J=21.3, 4.8), 4.84 (p, 1H, J=5.9), 4.64 (q, 1H, J=4.8), 4.30 (d, 1H, J=2.1), 4.21 (m, 1H), 4.00 (d, 2H, J=12.9), 3.12 (m, 1H), 2.719 (m, 4H), 2.430 (d, 2H, J=6.3), 2.272 (m, 2H), 2.00 (m, 2H), 1.77 (m, 2H), 1.56 (m, 2H), 1.207 (m, 2H), 0.68 (m, 1H), 0.50 (m, 1H).

LRMS ESI (M+H$^+$) 540.35.

HPLC: MeOH 20-95% gradient in water over 4 minutes at 40° C., 6 minutes total. Retention Time=3.04 min (6 min method).

Example 2

N-Cyclopropyl 2-{3-[1-((tetrahydrofuran-3-yloxy) carbonyl)piperidin-4-yl]propyn-1-yl}adenosine-5'-uronamide

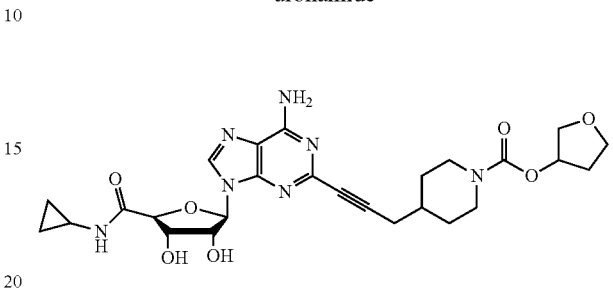

Tetrahydrofuran-3-yl 4-(prop-2-ynyl)piperidine-1-carboxylate (1.620 g, 6.83 mmol) was added to a solution of N-cyclopropyl 2-iodocarboxamidoadenosine (0.101 g, 0.226 mmol) according to general procedure for C-2 coupling provided in Example 1: yield 54 mg, 43%. LRMS ESI (M+H$^+$) 556.3. HPLC rt=6.0 min.

Example 3

N-Cyclopropyl 2-{3-[1-((tetrahydro-2H-pyran-4-yloxy)carbonyl)piperidin-4-yl]propyn-1-yl}adenosine-5'-uronamide

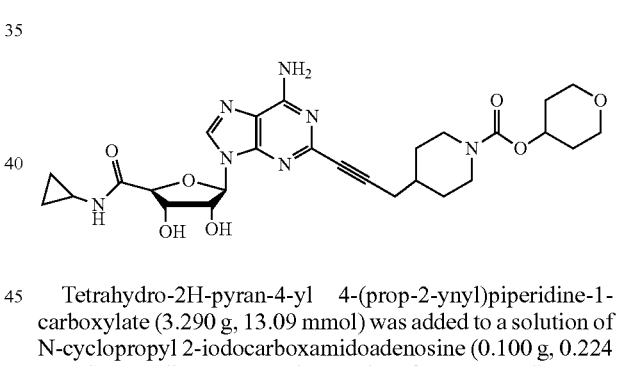

Tetrahydro-2H-pyran-4-yl 4-(prop-2-ynyl)piperidine-1-carboxylate (3.290 g, 13.09 mmol) was added to a solution of N-cyclopropyl 2-iodocarboxamidoadenosine (0.100 g, 0.224 mmol) according to general procedure for C-2 coupling provided in Example 1: yield 41 mg, 32%. LRMS ESI (M+H$^+$) 570.3. HPLC rt=6.5 min.

Cell culture and membrane preparation. Sf9 cells were cultured in Grace's medium supplemented with 10% fetal bovine serum, 2.5 µg/ml amphotericin B and 50 µg/ml gentamycin in an atmosphere of 50% N$_2$/50% O$_2$. Viral infection was performed at a density of 2.5×10$^6$ cells/mL with a multiplicity of infection of two for each virus used. Infected cells were harvested 3 days post-infection and washed twice in insect PBS (PBS pH 6.3). Cells were then resuspended in lysis buffer (20 mM HEPES pH 7.5, 150 mM NaCl, 3 mM MgCl$_2$, 1 mM β-mercaptoethanol (BME), 5 µg/mL leupeptin, 5 µg/mL pepstatin A, 1 µg/mL aprotinin, and 0.1 mM PMSF) and snap frozen for storage at −80° C. Cells were thawed on ice, brought to 30 mL total volume in lysis buffer, and burst by N$_2$ cavitation (600 psi for 20 minutes). A low-speed centrifugation was performed to remove any unlysed cells (1000×g for 10 minutes), followed by a high-speed centrifugation (17,000×g for 30 minutes). The pellet from the final centrifugation was homogenized in buffer containing 20 mM HEPES pH 8, 100 mM NaCl, 1% glycerol, 2 µg/mL leupeptin, 2 µg/mL pepstatin A, 2 µg/mL Aprotinin, 0.1 mM PMSF, and 10 µM GDP using a small glass homogenizer followed by passage through a 26 gauge needle. Membranes were aliquoted, snap frozen in liquid $N_2$, and stored at −80° C. Membranes from cells stably expressing the human $A_1$ AR (CHO K1 cells) or $A_3$ AR (HEK 293 cells) were prepared as described (Robeva et al., 1996).

Radioligand Binding Assays. Radioligand binding to recombinant human $A_{2A}$ receptors in Sf9 cell membranes was performed using either the radiolabeled agonist, $^{125}$I-APE (Luthin et al., 1995) or the radiolabeled antagonist, $^{125}$I-ZM241385 ($^{125}$I-ZM). To detect the high affinity, GTPγS-sensitive state of $A_1$ and $A_3$ AR, we used the agonist, $^{125}$I-ABA (Linden et al., 1985; Linden et al., 1993). Binding experiments were performed in triplicate with 5 µg ($A_{2A}$) or 25 µg ($A_1$ and $A_3$) membrane protein in a total volume of 0.1 mL HE buffer (20 mM HEPES and 1 mM EDTA) with 1 U/mL adenosine deaminase and 5 mM $MgCl_2$ with or without 50 µM GTPγS. Membranes were incubated with radioligands at room temperature for three hours (for agonists) or two hours (for antagonists) in Millipore Multiscreen® 96-well GF/C filter plates and assays were terminated by rapid filtration on a cell harvester (Brandel, Gaithersburg, Md.) followed by 4×150 µl washes over 30 seconds with ice cold 10 mM Tris-HCl, pH 7.4, 10 mM $MgCl_2$. Nonspecific binding was measured in the presence of 50 µM NECA. Competition binding assays were performed as described (Robeva et al., 1996) using 0.5-1 nM $^{125}$I-APE, $^{125}$I-ZM241385, or $^{125}$I-ABA. We found that it was sometimes important to change pipette tips following each serial dilution to prevent transfer on tips of potent hydrophobic compounds. The $K_i$ values for competing compound binding to a single site were derived from $IC_{50}$ values with correction for radioligand and competing compound depletion as described previously (Linden, 1982).

Linden J (1982) Calculating the Dissociation Constant of an Unlabeled Compound From the Concentration Required to Displace Radiolabel Binding by 50%. *J Cycl Nucl Res* 8: 163-172.

Linden J, Patel A and Sadek S (1985) [$^{125}$I]Aminobenzyladenosine, a New Radioligand With Improved Specific Binding to Adenosine Receptors in Heart. *Circ Res* 56: 279-284.

Linden J, Taylor H E, Robeva A S, Tucker A L, Stehle J H, Rivkees S A, Fink J S and Reppert S M (1993) Molecular Cloning and Functional Expression of a Sheep $A_3$ Adenosine Receptor With Widespread Tissue Distribution. *Mol Pharmacol* 44: 524-532.

Luthin D R, Olsson R A, Thompson R D, Sawmiller D R and Linden J (1995) Characterization of Two Affinity States of Adenosine $A_{2A}$ Receptors With a New Radioligand, 2-[2-(4-Amino-3-[$^{125}$I]Iodophenyl)Ethylamino]Adenosine. *Mol Pharmacol* 47: 307-313.

Robeva A S, Woodard R, Luthin D R, Taylor H E and Linden J (1996) Double Tagging Recombinant $A_1$- and $A_{2A}$-Adenosine Receptors With Hexahistidine and the FLAG Epitope. Development of an Efficient Generic Protein Purification Procedure. *Biochem Pharmacol* 51: 545-555.

Chemiluminescence Methods: Luminol enhanced chemiluminescence, a measure of neutrophil oxidative activity, is dependent upon both superoxide production and mobilization of the granule enzyme myeloperoxidase. The light is emitted from unstable high-energy oxygen species such as hypochlorous acid and singlet oxygen generated by activated neutrophils.

Purified human neutrophils (2×106/ml) suspended in Hanks balanced salt solution containing 0.1% human serum albumin (HA), adenosine deaminase (1 U/mL) and rolipram (100 nM) were incubated (37 C) in a water bath for 15 min with or without rhTNF (10 U/ml). Following incubation 100 L aliquots of the PMN were transferred to wells (White walled clear bottom 96 well tissue culture plates Costar #3670; 2 wells/condition) containing 501 HA and luminol (final concentration 100M) with or without adenosine agonist (final agonist concentrations 0.01-1000 nM). The plate was incubated 5 min (37 C) and then fMLP (50 l in HA; final concentration 1M) was added to all wells.

Peak chemiluminescence was determined with a Victor 1420 Multilabel Counter in the chemiluminescence mode using the Wallac Workstation software. Data are presented as peak chemiluminescence as percent of activity in the absence of an adenosine agonist. The EC50 was determined using PRISM software. All compounds were tested with PMNs from three separate donors.

Effect of $A_{2A}$ Agonists on Neutrophil Oxidative Activity: f-met-leu-phe (fMLP), luminol, superoxide dismutase, cytochrome C, fibrinogen, adenosine deaminase, and trypan blue were obtained from Sigma Chemical. Ficoll-hypaque was purchased from ICN (Aurora, Ohio), and Cardinal Scientific (Santa Fe, N. Mex.) and Accurate Chemicals and Scientific (Westerbury, N.Y.). Endotoxin (lipopolysaccharide; *E. coli* K235) was from List Biologicals (Campbell, Calif.). Hanks balanced salt solution (HBSS), and limulus amebocyte lysate assay kit were from BioWittaker (Walkersville, Md.). Human serum albumin (HSA) was from Cutter Biological (Elkhart, Ind.). Recombinant human tumor necrosis factor-α was supplied by Dianippon Pharmaceutical Co. Ltd. (Osaka, Japan). ZM241385 (4-(2-[7-amino-2-(2-furyl)-[1,2,4]triazolo[2,3-a][1,3,5]triazin-5-yl amino]ethyl)phenol) was a gift from Simon Poucher, Zeneca Pharmaceuticals, Cheshire, UK. Stock solutions (1 mM and 10 mM in DMSO) were made and stored at −20° C.

Human neutrophil preparation: Purified neutrophils (98% neutrophils and >95% viable by trypan blue exclusion) containing <1 platelet per 5 neutrophils and <50 pg/ml endotoxin (*limulus amebocyte* lysate assay) were obtained from normal heparinized (10 U/ml) venous blood by a one step Ficoll-hypaque separation procedure (A. Ferrante et al., *J. Immunol. Meth.*, 36, 109 (1980)).

Release of inflammatory reactive oxygen species from primed and stimulated human neutrophils Chemiluminescence: Luminol-enhanced chemiluminescence, a measure of neutrophil oxidative activity, is dependent upon both superoxide production and mobilization of the lysosomal granule enzyme myeloperoxidase. The light is emitted from unstable high-energy oxygen species generated by activated neutrophils. Purified neutrophils (5-10×10$^5$/ml) were incubated in Hanks balanced salt solution containing 0.1% human serum albumin (1 ml) with the tested $A_{2A}$ agonist with or without rolipram and with or without tumor necrosis factor α; (1 U/ml) for 30 minutes at 37° C. in a shaking water bath. Then luminol (1×10$^{-4}$ M) enhanced f-met-leu-phe (1 mcM) stimulated chemiluminescence was read with a Chronolog® Photometer (Crono-log Corp., Havertown, Pa.) at 37° C. for 2-4 minutes. Chemiluminescence is reported as relative peak light emitted (=height of the curve) compared to samples with tumor necrosis factor-α and without agonist or rolipram.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula II or a stereoisomer or pharmaceutically acceptable salt thereof:

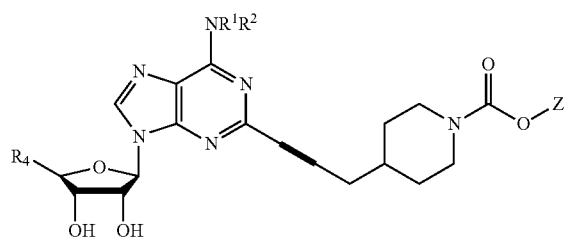

II wherein:
R¹ and R² independently are selected from H and $C_{1-3}$ alkyl;
Z is selected from cyclopropyl, cyclobutyl, cyclopentyl, tetrahydrofuranyl, azetidin-2-onyl, pyrrolidinyl, and pyrrolidin-2-onyl;
Z is substituted with 0-2 $Z^2$;
$Z^2$ is independently selected from F, $C_{1-4}$ alkyl, $CF_3$, $OCF_3$, $(CH_2)_aOR^3$, $(CH_2)_aNR^3R^3$, $NO_2$, $(CH_2)_aCN$, $(CH_2)_aCO_2R^3$, and $(CH_2)_aCONR^3R^3$;
$R^3$ is independently selected from H and $C_{1-6}$ alkyl;
$R^4$ is selected from $CH_2OR$ and C(O)NRR;
each R independently is selected from H, $C_{1-4}$ alkyl, cyclobutyl, and $(CH_2)_a$cyclopropyl; and
a is selected from 0, 1, and 2.

2. A compound according to claim 1, wherein:
R¹ and R² are H;
Z is substituted with 0-1 $Z^2$;
$Z^2$ is independently selected from F, $C_{1-2}$ alkyl, $CF_3$, $OCF_3$, and $OR^3$;
$R^3$ is independently selected from H and $C_{1-2}$ alkyl;
$R^4$ is C(O)NRR; and,
each R independently is selected from H, $C_{1-4}$ alkyl, cyclopropyl, cyclobutyl, and
—CH₂-cyclopropyl.

3. A compound or a stereoisomer or pharmaceutically acceptable salt thereof according to claim 1, wherein the compound is selected from:

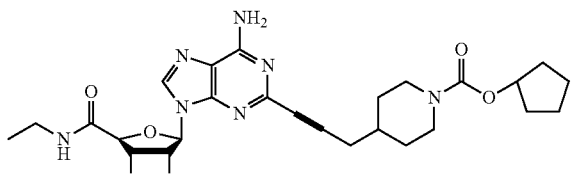

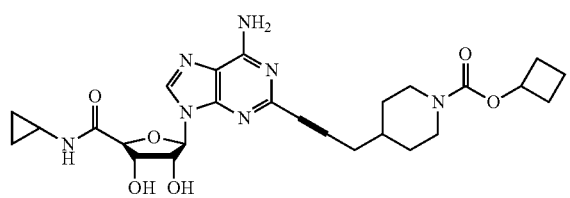

4. A compound or a stereoisomer or pharmaceutically acceptable salt thereof according to claim 1, wherein the compound is:

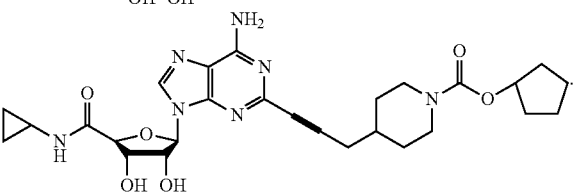

5. A compound or a stereoisomer or pharmaceutically acceptable salt thereof according to claim 1, wherein the compound is:

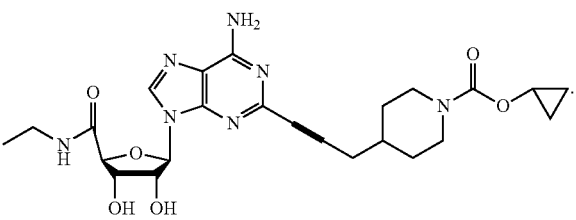

6. A compound or a stereoisomer or pharmaceutically acceptable salt thereof according to claim 1, wherein the compound is:

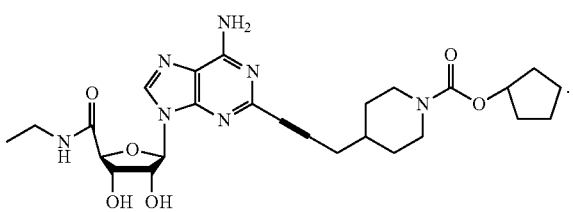

7. A compound or a stereoisomer or pharmaceutically acceptable salt thereof according to claim 1, wherein the compound is:

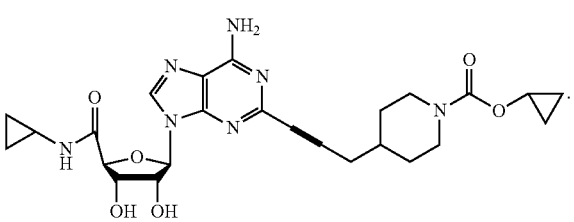

8. A compound or a stereoisomer or pharmaceutically acceptable salt thereof according to claim 1, wherein the compound is:

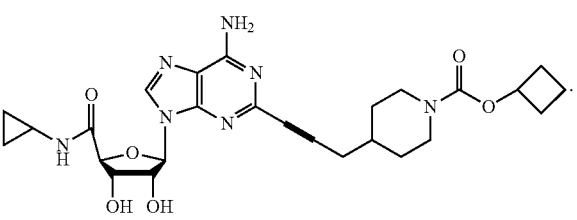

9. A compound or a stereoisomer or pharmaceutically acceptable salt thereof according to claim 1, wherein the compound is:

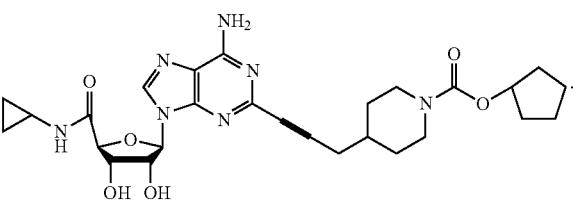

10. A pharmaceutical composition comprising a compound or a stereoisomer or pharmaceutically acceptable salt thereof according to claim 1, and a pharmaceutically acceptable carrier.

11. A pharmaceutical composition comprising a compound or a stereoisomer or pharmaceutically acceptable salt thereof according to claim 2, and a pharmaceutically acceptable carrier.

12. A pharmaceutical composition comprising a compound or a stereoisomer or pharmaceutically acceptable salt thereof according to claim 3, and a pharmaceutically acceptable carrier.

13. A pharmaceutical composition comprising a compound or a stereoisomer or pharmaceutically acceptable salt thereof according to claim 4, and a pharmaceutically acceptable carrier.

14. A pharmaceutical composition comprising a compound or a stereoisomer or pharmaceutically acceptable salt thereof according to claim 5, and a pharmaceutically acceptable carrier.

15. A pharmaceutical composition comprising a compound or a stereoisomer or pharmaceutically acceptable salt thereof according to claim 6, and a pharmaceutically acceptable carrier.

16. A pharmaceutical composition comprising a compound or a stereoisomer or pharmaceutically acceptable salt thereof according to claim 7, and a pharmaceutically acceptable carrier.

17. A pharmaceutical composition comprising a compound or a stereoisomer or pharmaceutically acceptable salt thereof according to claim 8, and a pharmaceutically acceptable carrier.

18. A pharmaceutical composition comprising a compound or a stereoisomer or pharmaceutically acceptable salt thereof according to claim 9, and a pharmaceutically acceptable carrier.

19. A method for treating inflammation comprising administering an effective anti-inflammatory amount of a compound or a stereoisomer thereof or pharmaceutically acceptable salt thereof according to claim 1.

20. A method of treating inflammation according to claim 19 wherein the inflammation is associated with one or more of the following conditions: (i) autoimmune disease, (ii) allergic disease, (iii) skin disease, (iv) infectious disease, (v) wasting disease, (vi) organ, tissue or cell transplantation, (vii) adverse effects from drug therapy, (viii) cardiovascular condition, (ix) gout, (x) dialysis, (xi) chemical trauma, (xii) thermal trauma, (xiii) sickle cell disease, (xiv) laminitis, (xv) founder's disease.

21. A method of treating inflammation according to claim 20 wherein the autoimmune disease is selected from the group consisting of lupus, multiple sclerosis, infertility from endometriosis, diabetes, Crohn's disease, ulcerative colitis, inflammatory bowel disease, osteoporosis and rheumatoid arthritis.

22. A method of treating inflammation according to claim 20 wherein the allergic disease is selected from the group consisting of asthma, hay fever, rhinitis, poison ivy and vernal conjunctivitis.

23. A method of treating inflammation according to claim 20 wherein the skin disease is selected from the group consisting of psoriasis, contact dermatitis, eczema, infectious skin ulcers, healing open wounds and cellulitis.

24. A method of treating inflammation according to claim 20 wherein the infectious disease is selected from the group consisting of sepsis, septic shock, encephalitis, infectious arthritis, endotoxic shock, gram negative shock, Jarisch-Herxheimer reaction, anthrax, plague, tularemia, ebola, shingles, toxic shock, cerebral malaria, bacterial meningitis, acute respiratory distress syndrome (ARDS), chronic obstructive pulmonary disease (COPD), lyme disease and HIV infection.

25. A method of treating inflammation according to claim 20 wherein the wasting disease is cachexia secondary to cancer or HIV.

26. A method of treating inflammation according to claim 20 wherein the organ, tissue or cell transplantation is associated with transplant rejection or graft versus host disease.

27. A method of treating inflammation according to claim 20 wherein the cardiovascular condition is a circulatory disease induced or exasperated by an inflammatory response.

28. A method of treating inflammation according to claim 20 wherein the cardiovascular condition is selected from the group consisting of ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis and cardiovascular complications of diabetes.

29. A method to diagnose myocardial perfusion abnormalities in a mammal comprising: (a) parenterally administering to said mammal an amount of a compound of claim 1; and (b) performing a technique on said mammal to detect the presence of coronary artery stenoses, assess the severity of coronary artery stenoses or both.

30. A method for treating a pathological condition or symptom in a subject, wherein the activity of $A_{2A}$ adenosine receptors is implicated and agonism of such activity is desired, comprising administering to the subject an effective amount of a compound of claim 1.

* * * * *